US009844594B2

(12) United States Patent
Antochshuk et al.

(10) Patent No.: US 9,844,594 B2
(45) Date of Patent: Dec. 19, 2017

(54) LIQUID FORMULATIONS FOR AN ANTI-TNF α ANTIBODY

(71) Applicant: MERCK SHARP & DOHME CORP., Rahway, NJ (US)

(72) Inventors: Valentyn Antochshuk, Cranford, NJ (US); Amardeep Bhalla, Montvale, NJ (US); Azher M. Hussain, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 13 days.

(21) Appl. No.: 14/653,555

(22) PCT Filed: Dec. 13, 2013

(86) PCT No.: PCT/US2013/074853
§ 371 (c)(1),
(2) Date: Jun. 18, 2015

(87) PCT Pub. No.: WO2014/099636
PCT Pub. Date: Jun. 26, 2014

(65) Prior Publication Data
US 2015/0329628 A1 Nov. 19, 2015

Related U.S. Application Data

(60) Provisional application No. 61/738,577, filed on Dec. 18, 2012.

(51) Int. Cl.
*A61K 39/395* (2006.01)
*C07K 16/24* (2006.01)

(52) U.S. Cl.
CPC ...... *A61K 39/39591* (2013.01); *C07K 16/241* (2013.01); *C07K 2317/21* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 5,869,050 A | * | 2/1999 | de Boer | A61K 39/395 424/133.1 |
| 8,871,201 B2 | * | 10/2014 | Li | A61K 9/2886 424/130.1 |
| 2006/0153846 A1 | | 7/2006 | Krause et al. | |
| 2009/0291062 A1 | | 11/2009 | Fraunhofer et al. | |
| 2010/0278822 A1 | | 11/2010 | Fraunhofer et al. | |
| 2010/0311643 A1 | * | 12/2010 | Bevec | A61K 38/22 514/1.5 |
| 2011/0300151 A1 | | 12/2011 | Okun et al. | |
| 2012/0263731 A1 | | 10/2012 | Fraunhofer et al. | |
| 2013/0315966 A1 | * | 11/2013 | Randolph | A61K 39/08 424/400 |

OTHER PUBLICATIONS

Anonymous: "Humira (adalimumab), Abbot Laboratories—Package Insert", Sep. 26, 2003 (Sep. 26, 2009), XP055405955, Retrieved from the Internet: URL:https://www.accessdata.fda.gov/drugsatfda_docs/label/2002/adalabb123102LB.htm [retrieved on Sep. 12, 2017].

* cited by examiner

*Primary Examiner* — Phillip Gambel
(74) *Attorney, Agent, or Firm* — Gloria M. Fuentes; Li Su

(57) ABSTRACT

The invention provides stable liquid formulations for a recombinant biopharmaceutical protein comprising a fully human anti-TNF monoclonal antibody.

4 Claims, 7 Drawing Sheets

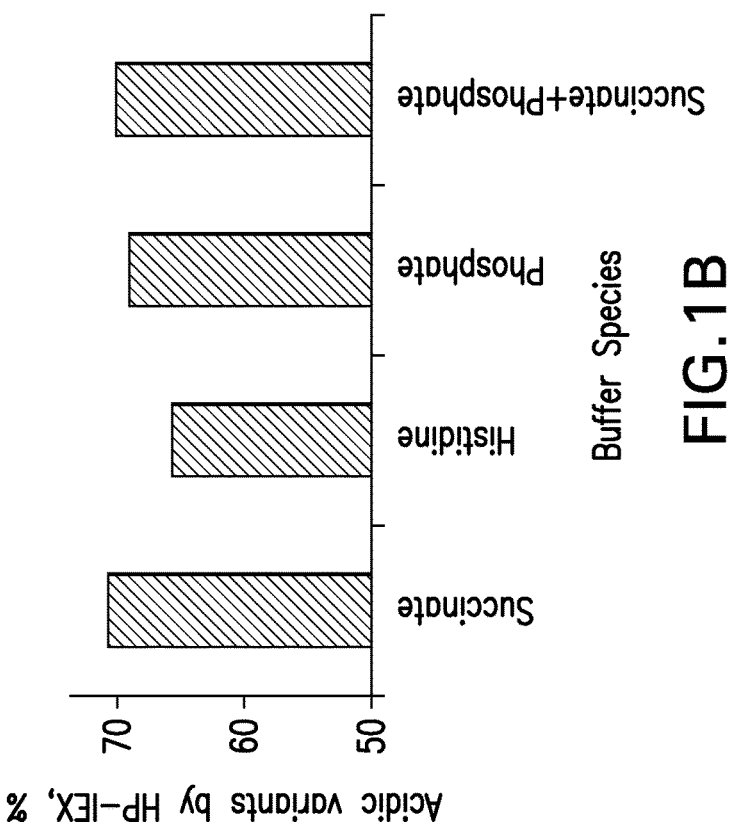
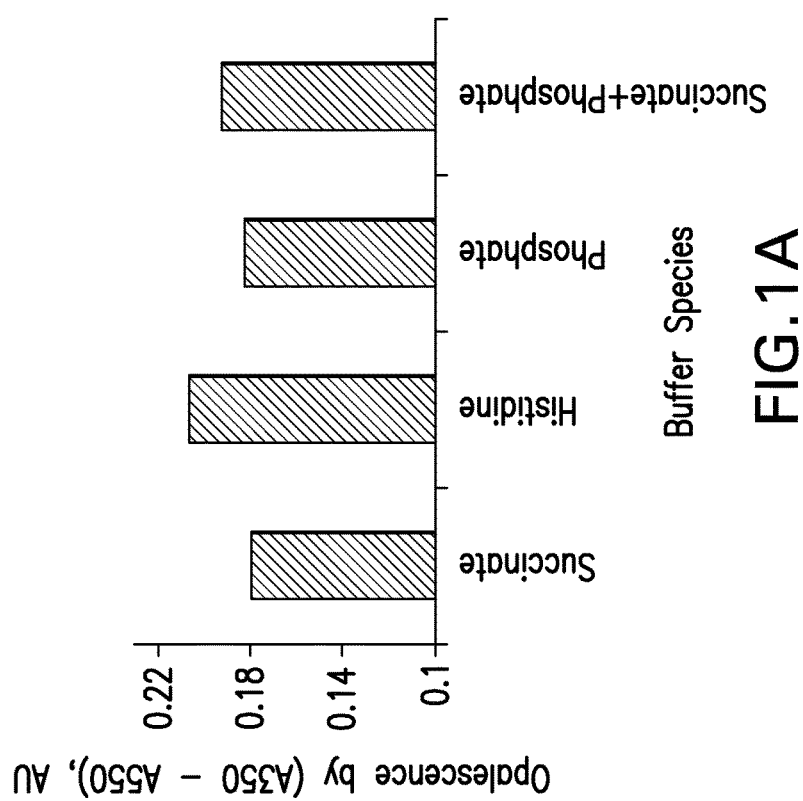

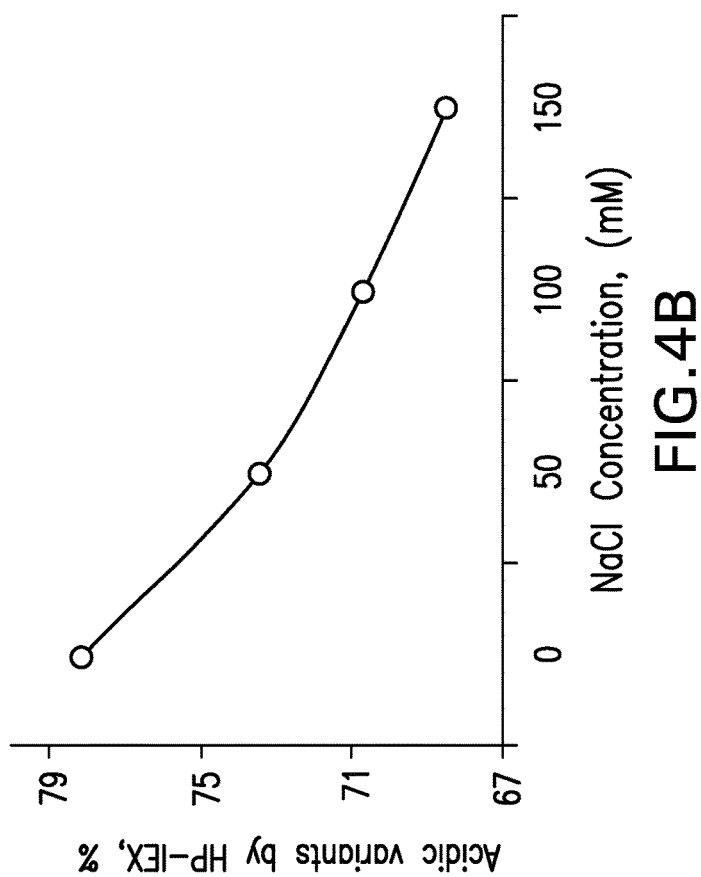
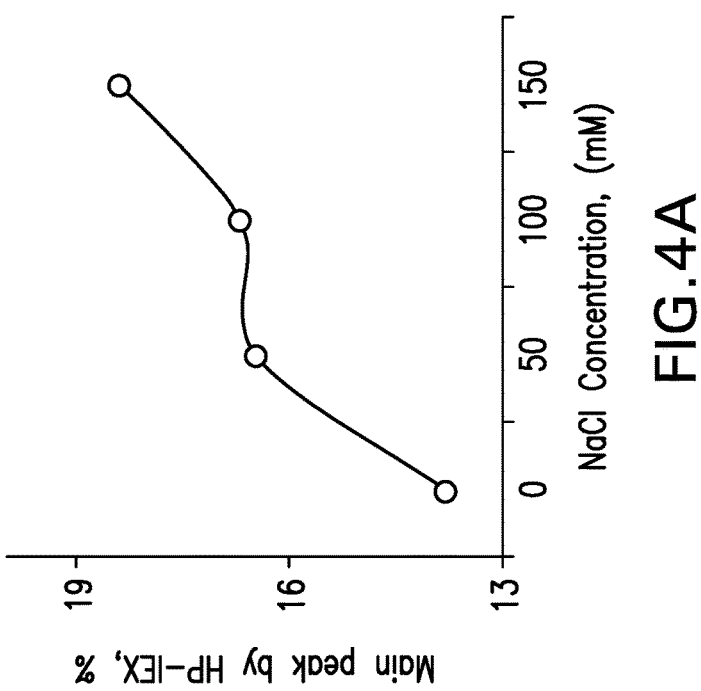
FIG. 4A
FIG. 4B

LIQUID FORMULATIONS FOR AN ANTI-TNF α ANTIBODY

FIELD OF THE INVENTION

The present invention relates to the field of biopharmaceutical protein formulation. More specifically, the invention provides stabilized liquid formulations for a recombinant biopharmaceutical protein comprising a fully human anti-TNF antibody.

BACKGROUND OF THE INVENTION

Typically, biopharmaceutical proteins such as monoclonal antibodies (mAbs) and are produced by recombinant DNA technology in mammalian cell expression systems. In order to guarantee the reproducible clinical performance of a biopharmaceutical product, manufacturers have to deliver a product of consistent and reproducible quality. It is well-established that molecular alterations can occur during every stage of the manufacturing process and that aspect of the upstream unit operations, including cell culture conditions, exposure to various buffers and solutions during the purification process and storage conditions, can each introduce heterogeneity into a monoclonal antibody (mAb) product.

Some of the molecular alterations can alter a quality attribute of a biopharmaceutical product, resulting in an undesirable change in the identity, strength or purity of the product. In addition, process-related heterogeneities can produce variant proteins characterized by alterations in either the size, chemical/charge or conformation of a biopharmaceutical protein. Furthermore, depending upon the type of host cell that is used, and the particular amino acid sequence of the protein, additional heterogeneity may also be introduced as a consequence of intracellular processes, such as post-translational modifications.

The primary goal of formulation development is to provide a pharmaceutical composition that will support the stability of a biopharmaceutical protein during all stages of its production, storage, shipping and use. The process of formulation development for an innovative biopharmaceutical protein, or a biosimilar antibody is essential to its safety, clinical efficacy and commercial success. Therefore, there is a need for stabilizing liquid (aqueous) formulations capable of mitigating these issues when a pharmaceutical composition comprising an antibody is stored, or marketed as a liquid product.

SUMMARY OF THE INVENTION

The present invention discloses stable liquid formulations comprising a fully human anti-TNF-α antibody. The disclosed formulations were developed in accordance with a defined set of selection criteria based on data collected from analytical procedures performed to evaluate the biochemical and biophysical stability of a fully human anti-TNF antibody in alternative formulations. Various buffer species and stabilizers were screened and salt and surfactant concentrations were optimized. A battery of rational biochemical/biophysical techniques was employed to identify and optimize buffer systems and excipients.

More specifically, the present invention provides stable liquid formulations for a fully human anti-TNF antibody referred to herein as biosimilar adalimumab, which do not comprise a buffer system that includes a citrate buffer. In one embodiment, the invention provides stable liquid pharmaceutical formulations comprising a phosphate buffer. For example, the invention provides stable liquid aqueous pharmaceutical formulation comprising an anti-TNF antibody, a pH-buffered phosphate solution, sodium chloride, a stabilizer and a surfactant, wherein the anti-TNF antibody is a biosimilar form of adalimumab. The disclosed phosphate-buffered formulations can comprise about 20 to 60 mg/mL of anti-TNF antibody. The pH of the disclosed pharmaceutical formulations is about pH 5.4.

In an alternative embodiment the invention provides liquid pharmaceutical formulations comprising a phosphate-succinate buffer, sodium chloride, a stabilizer and a surfactant, wherein the anti-TNF antibody is a biosimilar form of adalimumab. In alternative embodiments, the disclosed phosphate-succinate formulations can comprise about 20 to 60 mg/mL of anti-TNF antibody.

In various embodiments, stable aqueous (liquid) formulation can be prepared having a phosphate or phosphate-sucinate buffer with a desired pH (e.g., within the range of pH 5.0 to pH 5.7), sodium chloride (70 to 110 mM), a surfactant (e.g., PS80 0.1% w/v) and a stabilizer (mannitol or trehalose) comprising an effective amount of a fully human anti-TNF antibody. In particular embodiments, the antibody is a biosimilar form of adalimumab.

Another aspect of the invention provides a pre-filled syringe or autoinjector device, comprising any of the subject formulations described herein. In certain embodiments, the aqueous formulation stored in the pre-filled syringe or autoinjector device contains about 20 mg, or about 40 mg of a biosimilar adalimumab antibody. For example, the invention provides an autoinjector device containing a prefilled syringe comprising an aqueous formulation comprising a biosimilar form of adalimumab at a concentration of between about 20 and about 60 mg/mL, a phosphate buffer, sodium chloride, trehalose and polysorbate 80, wherein the pH of the formulation is about 5.4.

In an alternative embodiment, the invention provides an autoinjector device containing an aqueous formulation comprising a biosimilar form of adalimumab at a concentration of between about 20 and about 60 mg/mL, a phosphate buffer, sodium chloride, mannitol and polysorbate 80, wherein the pH of the formulation is about 5.4. In yet another embodiment, the invention provides an autoinjector device containing an aqueous formulation comprising a biosimilar form of adalimumab at a concentration of between about 20 and about 60 mg/mL, a phosphate and succinate buffer, sodium chloride, trehalose and polysorbate 80, wherein the pH of the formulation is about 5.4.

BRIEF DESCRIPTION OF THE DRAWINGS

FIGS. 1A-1B provides a graphic representation of the effect of buffer species on opalescence as estimated by a difference in absorption at 350 and 550 nm (FIG. 1A); and the effect of buffer species on % acidic variants as measured by HP-IEX (FIG. 1B).

FIG. 4A-4B provides a graphic representation of the effect of salt on % main peak (FIG. 4A) and % acidic peak (FIG. 4B), as measured by HP-IEX.

DETAILED DESCRIPTION

Figure 2:
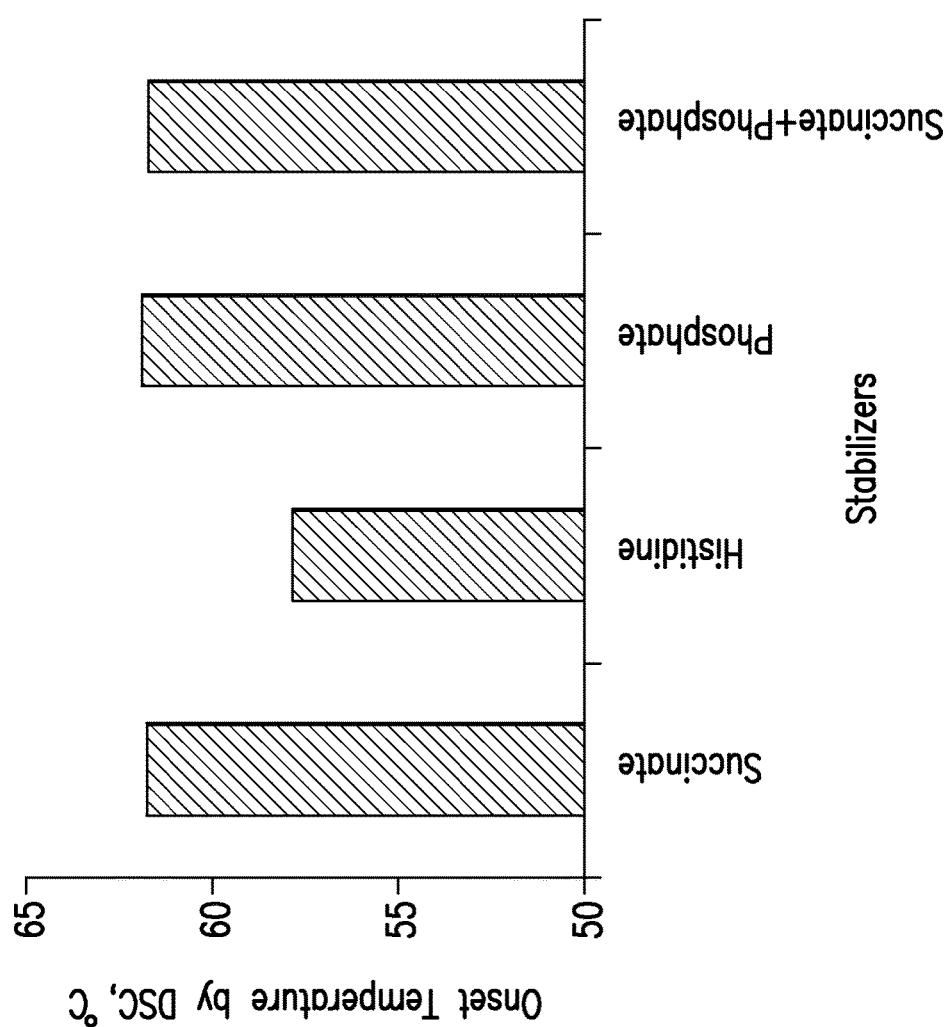
FIG. 2 provides a graphic representation of the effect of buffer species on the onset temperature as measured by DSC.

The following definitions are provided to facilitate understanding of certain terms used throughout the specification.

As used herein, the term "adalimumab," refers to a FDA approved fully humanized IgG1, TNF-alpha inhibitor monoclonal antibody (trade name Humira®) produced by Abbott Laboratories. Each IgG antibody molecule comprises two kappa light chains and two human IgG1 heavy chains, the total molecular weight of adalimumab is 148 kDa. Each light chain consists of 214 amino acid residues and each heavy chain consists of 451 amino acid residues. Adalimumab produced in CHO cells is characterized by a binding affinity of 100 mM to human TNFα, (U.S. Pat. No. 6,090,382, Human antibodies that bind human TNFα, Salfeld et al.)

As used herein, the term "biosimilar" is used in a manner that is consistent with the working definition promulgated by the US FDA which defines a biosimilar product to be one that is "highly similar" to a reference product (despite minor differences in clinically inactive components). In practice there can be no clinically meaningful differences between the reference product and the biosimilar product in terms of safety, purity, and potency (Public Health Service (PHS) Act §262). A biosimilar form of adalimumab is an antibody which a regulatory authority deems to be "highly similar" to the reference product Humira® on the basis of an abbreviated regulatory submission.

As used herein, the term "reference product," refers to Adalimumab (HUMIRA®). Generally speaking, reference products are "innovator products" comprising an approved biopharmaceutical product which has been approved by a regulatory authority for marketing in a geographical region subject to its jurisdiction on the basis of a full regulatory submission establishing the efficacy, quality and safety of the originator product.

As used here the term "anti-TNF antibody" refers broadly to any antibody having specificity for human TNF-α, including but not limited to adalimumab and a biosimilar form of adalimumab.

The term "human TNF-α" (abbreviated herein as hTNF-alpha, TNFcc, or simply hTNF), as used herein, is intended to refer to a human cytokine that exists as a 17 kDa secreted form and a 26 kDa membrane associated form, the biologically active form of which is composed of a trimer of noncovalently bound 17 kDa molecules. The structure of hTNF-alpha is described further in, for example, Pennica, D., et al. (1984) Nature 312:724-729; Davis, J. M., et al. (1987) Biochem 26: 1322-1326; and Jones, E. Y., et al. (1989) Nature 338:225-228.

As used herein, the phrase "stable" as it is used herein to refer to pharmaceutical compositions/formulations is a term of art and is used herein in accordance with its established meaning. In general the term refers to a composition in which a biopharmaceutical protein retains the physical, chemical and biological properties required by a regulatory agency for its approval. For example, a stable pharmaceutical composition is a formulation that between the time that is made and the time that it is used (or reaches the end of its intended shelf-life), does not undergo any changes in its physical, chemical or biological properties which renders it unsafe or ineffective for its intended pharmaceutical use. The meaning of the term is illustrated by the standards established in ICH Q5C, "Quality of Biotechnological Products: Stability Testing of Biotechnological/Biological Products," by the International Conference on Harmonization of Technical Requirements of Pharmaceuticals for Human Use, which is herein in incorporated by reference, particularly in parts pertinent to the stability of pharmaceutical compositions. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). In practice, stability can be measured at a selected temperature for a selected time period.

As used herein, "formulation" is a composition of a pharmaceutically active drug, such as a biologically active protein (e.g., mAb), that is suitable for parenteral administration (including but not limited to intravenous, intramuscular, or subcutaneous) to a patient in need thereof and includes only pharmaceutically acceptable excipients, diluents, and other additives deemed safe by the Federal Drug Administration or other foreign national authorities.

As used herein the phrases "liquid formulation" and "aqueous formulation" are used interchangeably to refer to a solution or liquid preparation that contains a biopharmaceutical in combination with one or more excipients (e.g., chemical additives)—dissolved in a suitable solvent.

The term "liquid formulation" refers to a formulation in a liquid state and is not intended to refer to reconstituted lyophilized formulations. A liquid formulation of the invention is stable upon storage, and does not rely upon lyophilization (or other state change methods, e.g., spray drying) for stability.

The term "liquid aqueous formulation" refers to a liquid formulation using water as a solvent. In one embodiment, a liquid aqueous formulation is a formulation that maintains stability {e.g., chemical and/or physical stability/and/or biological activity) without the need for lyophilization, spray-drying, and/or freezing.

The term "pharmaceutical," as used herein, refers to a composition, e.g., an aqueous formulation, that it is useful for treating a disease or disorder.

The term "pharmaceutically acceptable" is used herein in accordance with its well-known meaning in the art to denote that which is acceptable for medical or veterinary use, preferably for medical use in humans, particularly approved for use by the US Food and Drug Administration or other regulatory authority.

As used herein, the phrase "pharmaceutical composition" refers to a formulation such that it is suitable for administration and/or injection into a human patient in need thereof. The term "pharmaceutical formulation" refers to preparations which are in such form as to permit the active ingredients to be effective, and which contains no additional components which are toxic to the subjects to which the formulation would be administered.

A "stable" biosimilar adalimumab formulation is a pharmaceutical formulation with no significant changes observed at a refrigerated temperature of (2-8° C.) for at least 3 months, preferably 6 months, and more preferably 1 year, and even more preferably up through 2 years. Stability of the formulations disclosed herein can be evaluated using the following criteria: 1) the aqueous formulation is colorless, or clear to slightly opalescent by visual analysis; 2) the protein content is between 45.0 to 55.0 mg/mL; 3) the pH is maintained within +/−0.2 pH units from target pH; 4) the percent of monomer by SEC is ≥95%; 5) the Purity as measured by CE-SDS is ≥93% and the relative potency based on ELISA is within 70-150%.

As used herein, the term "buffer" encompasses those agents which maintain the solution pH in an acceptable range. A buffer is an aqueous solution consisting of a mixture of a weak acid and its conjugate base or a weak base and its conjugate acid. Its pH changes very little when a small amount of strong acid or base is added to it and thus it is used to prevent any change in the pH of a solution. Buffer solutions are used in protein formulations as a means of keeping proteins within a narrow pH range to optimize shelf life. As used herein, the term "buffer" refers to a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975).

The buffer of this invention has a pH in the range from about 4.9 to about 5.7, more preferably in the range from about pH 5.3 to about 5.5. In particular embodiments, the pH of the stable liquid aqueous pharmaceutical formulations of the invention have a pH of about 5.2, 5.3, 5.4, 5.5, or 5.6. Examples of buffers that will control the pH in this range include acetate, citrate, gluconate, glutamate, histidine, phosphate, succinate and other organic acid buffers.

As used herein the term "excipient" is intended to mean a therapeutically inactive substance. Excipients are included in a formulation for a wide variety of purposes, for example, as a buffer, stabilizer, tonicity agent, surfactant, anti-oxidant, cryoprotectant or diluent.

Suitable excipients include, but are not limited to polyols (also known as sugar alcohols) such as mannitol or sorbitol, sugars such as sucrose, lactose or dextrose, salts such as NaCl, KCl or calcium phosphate, amino acids, for example, histidine, lysine, aspartic acid, or glutamic acid, surfactants, as well as water. The purity of the excipient should meet compendial standards (e.g., USP, EP, JP) and be of sufficient purity for subcutaneous, intramuscular, or intravenous injection into humans.

Various literature references are available to facilitate selection of pharmaceutically acceptable carriers or excipients. See, e.g., Remington's Pharmaceutical Sciences and U.S. Pharmacopeia: National Formulary, Mack Publishing Company, Easton, Pa. (1984); Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman et al. (eds.) (1990) Pharmaceutical Dosage Forms: Disperse Systems, Marcel Dekker, NY; Weiner, Wang, W., Int. J. Pharm. 185:129-188 (1999) and Wang, W., Int. J. Pharm. 203:1-60 (2000), and Kotkoskie (2000) Excipient Toxicity and Safety, Marcel Dekker, Inc., New York, N.Y.

As used herein the term "tonicity agent" refers to an agent which functions to render a solution similar in osmotic characteristics to physiologic fluids. For example, Dextrose, Mannitol, Sodium Chloride, Potassium chloride and Glycerin are typically used in protein formulations as tonicity agents to render the parenteral product solutions "isotonic" with body fluids.

The term "isotonic" means that the formulation of interest has essentially the same osmotic pressure as human blood. Isotonic or physiologic formulations will generally have an osmotic pressure from about 275-325 mOsm. Slightly hypotonic pressure is 250-270 and slightly hypertonic pressure is 330-350 mOsm. Osmotic pressure can be measured, for example, using a vapor pressure or freezing point depression type osmometer. Typically, particular excipients, referred to in the field as "tonicity modifiers" or "tonicity agents" are used to control the tonicity of a pharmaceutical formulation. Salts (NaCl, KCl, MgCl2, CaCl2, etc.) represent commonly used as tonicity modifiers. In addition, excipients such as, but not limited to sucrose, mannitol, trehalose, glycine, etc. can function as tonicity modifiers.

"Pharmaceutically acceptable" excipients (vehicles, additives) are those which can reasonably be administered to a subject mammal to provide an effective dose of the active ingredient employed.

The aggregate content can be determined using High Performance Size Exclusion chromatography (HP-SEC), which separates molecules based on size. The early eluting peak corresponds to high molecular weight species or % aggregates. The main peak (intact protein) corresponds to % monomer. The late eluting peak corresponds to low molecular weight species or % fragments.

As used herein, the term "acidic variant" refers to a variant of a target protein which is more acidic (e.g. as determined by cation exchange chromatography) than the target protein. An example of an acidic variant is a deamidated variant.

An antibody protein "retains its biophysical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

As used herein the term "opalescence" refers to an optical phenomenon that arises from visible light scattering by solutes present in a solution. Moderate to high concentrations of protein solutions often exhibit opalescence or mild form of turbidity due to scattering of visible light. An opalescent appearance in a concentrated protein solution may result from a variety of factors. When a therapeutic protein (e.g., therapeutic mAbs) is susceptible to opalescence, the opalescent appearance usually increases as the protein concentration increases. The similarity of opalescent solutions to aggregated protein solutions has raised concerns with respect to its loss of protein activity and potential to cause immunogenicity in pharmaceutical formulations.

An antibody "retains its biochemical stability" in a pharmaceutical formulation, if it shows no significant chemical alteration. Chemical stability can be assessed by detecting and quantifying chemically altered forms of the protein.

Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody protein "retains its biological activity" in a pharmaceutical formulation, if the biological activity of the fusion protein at a given time is within a predetermined range of the biological activity exhibited at the time the pharmaceutical formulation was prepared. The biological activity of an anti-TNF antibody can be determined, for example, by a TNF binding assay. Specifically, an ELISA (enzyme-linked immunosorbent assay) is used to directly measure the interactions of the anti-TNF antibody and TNF-$\alpha$ extracellular domain. The assay is run in a direct binding manner such that a constant amount of TNF-$\alpha$ is adsorbed onto a 96 well plate, after which anti-TNF-$\alpha$ sample is serially diluted across the plate to allow the binding between varying amounts of sample in solution to the fixed amount of TNF-$\alpha$ on the plate. Another potency assay which can be used is a cell-based assay. A cell-based assay is a functional in vitro potency assay which measures biological activity. In this instance, the ability of the anti-TNF-$\alpha$ antibody to neutralize 50% apoptosis in the presence of A375 cells is translated into potency units.

As used herein the term "potency" refers to the specific ability or capacity of the product, as indicated by appropriate laboratory tests, to yield a given result. In the case of biologics, potency will help establish structure-function correlations, assist in determining immunologic response, and elucidate the molecule's biological identity.

As used herein the term "accelerated stability study" refers to a stability study conducted under conditions (e.g., 40° C. temperature) designed to increase the rate of chemical degradation or physical change of a Drug Substance (DS)/Active Pharmaceutical Ingredient (API) or Drug Product (DP) using exaggerated storage conditions. The purpose of the study is to monitor any degradation reactions which than will help to predict the shelf life of a Drug Substance (API) or Drug Product (DP) under the defined storage conditions.

The "isoelectric point" or "pI" of a protein is the pH at which the protein has a net overall charge equal to zero, i.e., the pH at which the protein has an equal number of positive and negative charges. Determination of the pI for any given protein can be done according to well-established techniques, such as, e.g., by isoelectric focusing. Isoelectric focusing is a technique for separating different molecules by differences in their isoelectric point (pI). It is a type of zone electrophoresis, usually performed on proteins in a gel that takes advantage of the fact that overall charge on the molecule of interest is a function of the pH of its surroundings.

The terms "AUC," "Cmax," and "Tmax" are used in herein in accordance with their normal meaning to refer to pharmacokinetic parameters that may be used to characterize the pharmacokinetic responses of a particular drug product in an animal or human subject. The term "AUC" refers to the "area under the curve" that represents changes in blood, serum, or plasma concentrations of a substance, e.g., a human anti-TNF antibody, over time. As used herein, the term "Cmax" refers to the maximum or peak blood, serum, or plasma concentration of substance observed in a subject after its administration. The term "Tmax" refers to the time at which the Cmax occurred, as measured from the time point of administration."

As used herein, "shelf life" means that the storage period during which an active ingredient such as a therapeutic protein in a pharmaceutical formulation has minimal degradation (e.g., not more than about 2-3% degradation) when the pharmaceutical formulation is stored under specified storage conditions, for example, 2-8° C.

As used herein, the terms "about" or "approximately" used with a pH or pi (isoelectric point) value refers to a variance of 0.1, 0.2, 0.3, 0.4 or 0.5 units. When used with a temperature value, "about" or "approximately" refers to a variance of 1, 2, 3, 4 or 5 degrees. When used with other values, such as length and weight, "about" or "approximately" refers to a variance of 1%, 2%, 3%, 4% or 5%. As used herein the term "about" is understood to mean that there can be variation in the concentration of a component of the described formulation which can encompass a range from 5%, 10%, 15% or up to and including 20% of the given value. For example, if a formulation has about 25 mg of an excipient, it may include an amount ranging from 20 mg to 30 mg.

It should be understood that while various embodiments are presented using "comprising" language, under various circumstances, a related embodiment may also be described using "consisting of" or "consisting essentially of" language. The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition.

It should be understood that when describing a range of values, the characteristic being described could be an individual value within the range. For example, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH.

Throughout this application, various publications (including patents and patent applications) are referenced. The disclosures of these publications in their entireties are hereby incorporated by reference. The references cited in the present application are not admitted to be prior art to the claimed invention.

Formulation Development

Formulation development is a considered to be a downstream unit operation which is focused on ensuring that the final product is conferred with a level of stability that will guarantee its safety and efficacy for the duration of its shelf-life. The development of an innovative or biosimilar mAb product for administration to human subjects requires a comprehensive characterization of its structural integrity, purity, and stability. The successful development of a robust formulation requires an understanding of the physical and chemical characteristics of the biopharmaceutical protein and the inactive ingredients alone and in combination. Inherent protein properties such as its tendency for self-association/aggregation, solubility and viscosity in solution pose challenges to the development of high concentration formulations. Achieving a suitable formulation requires an integrated approach whereby a stable formulation is developed that can be successfully administered and economically manufactured.

Generally speaking, formulation development involves optimizing the excipients present in a pharmaceutical composition (liquid or lyophilized powder) in order to minimize the physical (denaturation, aggregation) and/or chemical (oxidation, deamidation, isomerization, hydrolysis) degradation of the antibody. In drug formulation, the safety of the excipients present in a pharmaceutical composition is as important as the safety of the active product ingredient.

Formulation development of a biopharmaceutical glycoprotein for therapeutic use presents distinct challenges not encountered during the formulation of synthetic small molecule agents. This is partially attributed to the considerations noted above regarding the inherent heterogeneity which characterizes the biological processes used to manufacture these types of therapeutic agents. It is also attributed to the fact that antibodies and Fc-containing fusion proteins are complex molecules characterized by a multi-domain three-dimensional structure composed of numerous reactive chemical groups. In addition, mAbs and Fc-fusion proteins are typically administered at relatively high doses (i.e., on the order of mg/kg), or via routes (i.e., subcutaneous), which requires that the use of a small (i.e., ≤1.5 mL) dose volume. In practice, typical concentration requirements for monoclonal antibodies and Fc-containing fusion proteins can range from 5 mg/mL to higher than 25 mg/mL. The development of high protein concentration formulations also facilitate the use of delivery options, such as prefilled syringes and autoinjector devices which are both amenable to chronic administration and which could improve patient compliance. These doses are significantly higher than those required for other classes of therapeutic proteins such as growth factors, clotting factors and cytokines or interleukins. Not surprisingly, the task of formulating a biological pharmaceutical at relatively high concentrations (e.g., >25 mg/mL) poses unique challenges.

Using anyone of the stable liquid formulations disclosed herein, stability of the biosimilar anti-TNF antibody protein can be assessed using methods known in the art, including but not limited to size exclusion chromatography, cation chromatography, particle counting and in vitro binding and/or functional assays. Generally speaking biochemical and/or physiochemical activity can be assessed at two or more time points to determine the stability of the anti-TNF antibody in the formulation. It should be noted that the retention of structure and/or function and/or biological activity does not have to be 100%. Measurement of the stability of a formulation is a comparative exercise.

Therefore, if one formulation is said to be more stable, or have greater stability than another, the formulation with the greater stability has retained a higher percentage of a desired structural or functional characteristic that the other formulation(s). For example, formulation A is more stable than formulation B if it maintains a greater percentage of the main peak when measured by size exclusion chromatography (i.e., it is characterized by a lower degree of aggregation).

The formulations disclosed herein were selected in accordance with a defined set of criteria developed to ensure that the safety, purity, and potency of a biosimilar drug product comprising adalimumab would be highly similar to the corresponding features of the reference product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

For example, the optimal pH, buffer system and excipients were selected herein on the basis of biochemical stability data collected from accelerated stability studies primarily on the basis of minimizing the change in opalescence; minimizing the percentage of aggregates and fragments; and maximizing the percentage of monomer. CE-SDS data was used as an orthogonal method to SEC-HPLC to monitor product quality. Data from intrinsic fluorescence and light scattering studies was also utilized to corroborate primary selection criteria described above.

In some embodiments, stability of a formulation includes, for example retention of biological activity. Biological activity can be assessed using, for example an in vitro, in vivo and/or in situ assay indicative of the biopharmaceutical's function. Retention of stability of a biopharmaceutical in a formulation of the invention can include, for example, retention of activity between 80 and about 100% or more, depending on the inherent variability in the assay. For example, retention in stability can include retention of activity between about 80% to about 99% or between about 85% to about 95% compared to the activity of the biopharmaceutical at an initial time point. Generally speaking, an initial time point is selected to be the time that a biopharmaceutical is first prepared in a formulation or first examined for quality (for example a determination of if it meets release specifications).

Analytical methods suitable for evaluating the product stability include size exclusion chromatography (SEC), dynamic light scattering test (DLS), differential scanning calorimetery (DSC), iso-asp quantification, potency, UV at 350 nm, UV spectroscopy, and FTIR. SEC (J. Pharm. Scien., 83:1645-1650, (1994); Pharm. Res., 11:485 (1994); J. Pharm. Bio. Anal., 15:1928 (1997); J. Pharm. Bio. Anal., 14:1133-1140 (1986)) measures percent monomer in the product and gives information of the amount of soluble aggregates. DSC (Pharm. Res., 15:200 (1998); Pharm. Res., 9:109 (1982)) gives information of protein denaturation temperature and glass transition temperature. DLS (American Lab., November (1991)) measures mean diffusion coefficient, and gives information of the amount of soluble and insoluble aggregates. UV at 350 nm measures scattered light intensity at 350 nm and gives information about the amounts of soluble and insoluble aggregates. UV spectroscopy measures absorbance at 280 nm and gives information of protein concentration. FTIR (Eur. J. Pharm. Biopharm., 45:231 (1998); Pharm. Res., 12:1250 (1995); J. Pharm. Scien., 85:1290 (1996); J. Pharm. Scien., 87:1069 (1998)) measures IR spectrum in the amide one region, and gives information of protein secondary structure.

Each biopharmaceutical protein has unique characteristics that affects its solvent interaction, stability, hydrophobicity, and folding. The "structural differences among different proteins are so significant that generalization of universal stabilization strategies has not been successful" (Wang, W., Intl. J. Pharm. 185:129 (1999)). One of the most challenging tasks in the development of an aqueous or liquid formulation for a biopharmaceutical protein is dealing with its physical and chemical instabilities in a manner which preserves its biological activity for an acceptable shelf life. In practice the development of a formulation which confers stability to a particular biopharmaceutical protein requires balancing between destabilizing and stabilizing forces.

The US Food and Drug Administration (FDA) and the European Medicines Agency (EMA) have published draft guidelines indicating a willingness to approve biosimilar drug products that have a different formulation than its reference product, provided that the licensing application contains sufficient information to establish that the biosimilar product is "highly similar" to the reference product notwithstanding minor differences in clinically inactive components. In addition, biosimilar applicants will also have to satisfy the prong of the comparability assessment that requires proof that there are no clinically meaningful differences between the biosimilar product and the reference product in terms of safety, purity, and potency (FDA Biosimilar Draft Guidance: Questions and Answers Regarding Implementation of the Biologics Price Competition and Innovation Act of 2009, Part I Biosimilarity or Interchangeability, Q.I.3). The EMA has commented that the applicant "should take into account state-of-the-art technology and, regardless of the formulation selected, the suitability of the proposed formulation with regards to stability, compatibility (i.e. interaction with excipients, diluents and packaging materials), integrity, activity and strength of the active substance should be demonstrated" (Guideline on similar biological medicinal products containing biotechnology-derived proteins as active substance: quality issues (draft, revision 1) EMA/CHMP/BWP/247713/2012).

To date, there are no established criteria describing how the Food and Drug Administration (FDA) will require a biosimilar applicant to establish that a particular biopharmaceutical product is "highly similar" to a reference product. The statutory definition provides that a biosimilar product can have minor differences in clinically inactive components, provided that "there are no clinically meaningful differences between the biological product and the reference product in terms of the safety, purity, and potency of the product" (42 USC §262(i)(1)). An "inactive ingredient" is any component of a drug product other than the active ingredient. In practice excipients and stabilizers are inactive ingredients of pharmaceutical compositions. In the absence of guidance from the regulatory authorities, it is not clear if the "highly similar" standard will tolerate the same types of differences in quality attributes as the comparability standard. However, it is clear that there is a need for alternative pharmaceutical compositions comprising adalimumab prepared in alternative formulations.

Adalimumab

Adalimumab (HUMIRA®, Abbott Laboratories, Abbott Park, Ill., USA) is a fully human recombinant antibody which binds to human TNF-α. It was approved by the US Food and Drug Administration (FDA) in 2002 and by the European Agency for the Evaluation of Medical (EMEA) Products in 2003 for the treatment of rheumatoid arthritis. It was subsequently approved for the treatment of other TNF-mediated chronic inflammatory diseases, including psoriatic arthritis, chronic plaque psoriasis, ankylosing spondylitis, Crohn's disease and polyarticular juvenile idiopathic arthritis. It can be used alone or in combination with methotrexate (MTX) or other nonbiological disease modifying anti-rheumatic drugs (DMARDs).

Adalimumab was derived from murine monoclonal antibody MAK195 using guided selection phage display. The fully human, affinity matured clone D2E7, comprises human-derived heavy and light chain variable regions and a human IgG 1 kappa (κ) constant region. Each IgG antibody molecule comprises two kappa light chains and two human IgG1 heavy chains, the total molecular weight of adalimumab is 148 kDa. Each light chain consists of 214 amino acid residues and each heavy chain consists of 451 amino acid residues. The amino acid sequences of the variable heavy and light chains are known. For example, the amino acid sequence of the heavy chain variable region of adalimumab is disclosed in U.S. Pat. No. 6,090,382 (Human Antibodies the Bind TNFα). The amino acid sequence of the light chain variable region is also disclosed in U.S. Pat. No. 6,090,382). The full length (e.g., variable heavy and constant heavy) heavy chain amino acid sequence is disclosed as the protein product that is encoded by an expression vector disclosed in WO2007/014162 (Multiple Gene Expression Including sORF Constructs and Methods with Polyproteins, Pro-proteins and Proteolysis). The full length (variable light and constant light) light chain amino acid sequence is disclosed in WO2008057240 (Crystalline anti-TNFα Antibodies).

For the treatment of rheumatic diseases, adalimumab is typically administered by subcutaneous injection at 40 mg every one or two weeks. It is supplied in glass vials, prefilled glass syringes and as an autoinjection device called HUMIRA® Pen, as a sterile, preservative-free solution for subcutaneous administration. The solution of HUMIRA® is clear and colorless with a pH of about 5.2. The prefilled syringes and autoinjector comprise 40 mg of adalimumab in 0.8 mL of a buffered solution of mannitol, citric acid monohydrate, sodium citrate, disodium phosphate dihydrate, monosodium phosphate dihydrate, sodium chloride and Polysorbate 80. More specifically, each 0.8 mL HUMIRA® dose contains 40 mg of adalimumab in the presence of the excipients listed in Table 1.

TABLE 1

| Commerical Formulation |
|---|
| 40 mg Adalimumab |
| 4.93 mg Sodium Chloride |
| 0.69 mg monobasic sodium phosphate dihydrate |
| 1.22 mg dibasic sodium phosphate dihydrate |
| 0.24 mg sodium citrate |
| 1.04 mg citric acid monohydrate |
| 9.9 mg mannitol |
| 0.8 mg Polysorbate 80 |

U.S. Pat. No. 8,216,583 (Formulations of Human Antibodies for Treating TNF-α Associated Disorders) (referred to herein as the '583 patent, equivalent of EP 1528933 and WO 2004/016286) (assigned to Abbott Biotechnology Ltd) discloses the commercial liquid formulations currently used for adalimumab. The '583 patent discloses a formulation suitable for stabilizing solutions comprising adalimumab at a high concentration (e.g., ranging from about 1 to about 150 mg/ml) for long term storage (at least about 18 months) comprising a buffer system which contains a phosphate and citrate buffer to maintain a pH in the range of about 4 to about 8, a salt (sodium chloride), a polyol, (such as mannitol), and a surfactant, (polysorbate 80). The '583 patent indicates that the mannitol and the sodium chloride present in the formulation function as a tonicity agent.

The '583 patent further indicates that preferably, the aqueous formulation is isotonic, and that the amount of polyol that is added to the formulation may vary with respect to the desired isotonicity of the formulation. In the most preferred embodiment disclosed in the '583 patent, the polyol is mannitol at a concentration of about 10-14 mg/ml.

The '583 patent further indicates that a detergent or surfactant is also included in the HUMIRA® formulation, in order to reduce aggregation of the formulated antibody and/or to minimize the formulation of particulates and/or to reduce adsorption. In a preferred embodiment about 0.1% of polysorbate 80 is included in the art-recognized formulation.

U.S. Patent Publication No. 2009/0291062 A1 (Protein Formulations and Methods of Making Same) (referred to herein as Fraunhofer (2009)), equivalent of EP 2231175 and WO 2009/073569) discloses alternative formulations for adalimumab. The compositions disclosed in Fraunhofer (2009) provide aqueous protein formulations which comprise high concentration of adalimumab and water in the absence of additional agents/excipients. The disclosed formulations are prepared using a specific diafiltration/ultrafiltration process and pure water as an exchange medium, having a determined volume exchange (e.g., a five fold volume exchange with the water). The disclosure indicates that the formulations of the invention do not require excipients, such as for example surfactants or buffering systems, where are used in traditional formulations (e.g., including the present commercial formulation for HUMIRA® discussed above in the context of the '583 patent). The Fraunhofer (2009) formulations are described as having low conductivity (e.g., less than about 2.5 mS/cm) and low osmolality (e.g., no more than about 15 mOsmol/kg) as a consequence of the absence of ionic (or ionizable) excipients and the formulated proteins are characterized as having a hydrodynamic diameter (Dh) which is at least about 50% less than the Dh of the protein in a buffered solution at the given concentration. In some embodiments, the aqueous formulations comprising adalimumab disclosed in Fraunhofer (2009) comprise a non-ionic excipient. Example 22, describes stability studies conducted on formulations comprising adalimumab formulated in water and non-ionic excipients, such as a sugar alcohol (e.g., mannitol or sorbitol), or a sugar (e.g., sucrose, trehalose, raffinose or maltose).

U.S. Patent Publication No. 2010/0278822 A1 (Stable High Protein Concentration Formulations of Human Anti-TNFα Antibodies) (referred to herein as Fraunhofer (2010)), equivalent of WO 2010/0278822) discloses alternative formulations for adalimumab. The compositions disclosed in Fraunhofer (2010) provide alternative art-known high-concentration formulations of adalimumab. The publication indicates that the disclosed formulations are established, at least in part, on the surprising finding that adalimumab will remain soluble in a high concentration (e.g., 100 mg/ml) non-aggregated, and chemically stable (e.g., no oxidation or deamidation) form over a wide pH range (e.g., about pH 5.2 to about pH 6.0) in a formulation which does not include sodium chloride (NaCl) as a stabilizer. Fraunhofer 2010 indicates that the disclosed formulations have improved properties compared to other art-recognized formulations for adalimumab, and that the invention disclosed in the 2010 publication is based on the surprising finding that by removing NaCl and adding more than 20 mg/mL of a polyol, e.g., a sugar alcohol (mannitol or sorbitol), the concentration of a human TNF alpha antibody in a formulation can be increased to about 100 mg/ml while maintaining a viscosity that is suitable for subcutaneous administration without significant pain at the injection site. Fraunhofer 2010 indicates that polyol-induced stabilization of adalimumab was impeded by the presence of NaCl, and that as a sole excipient NaCl did not increase protein stability. In particular embodiments of the Fraunhofer 2010 publication, the formulations comprise a buffer system which contains citrate and/or phosphate to maintain the pH in a range of about 5.0 to about 6.4.

Other art-recognized formulations for adalimumab include the formulations disclosed in US 2012-0263731 A1 (High Concentration Anti-TNFα Antibody Liquid Formulations) (referred to herein as Fraunhofer (2012), equivalent of WO2012/065072. Fraunhofer 2012 discloses liquid aqueous formulations comprising adalimumab, a surfactant; and a polyol, in a formulation which does not contain a buffer or a salt. Formulations of the invention containing a polyol preferably contain less than about 50 mg of the polyol. In one of the disclosed embodiments, the formulations contain less than about 45 mg/mL of the polyol. In another embodiment, the formulations of the invention contain about 38-46 mg/mL of the polyol (e.g., mannitol). In a particular embodiment, Fraunhofer 2012 described a pharmaceutical formulation which contains adalimumab (or a biosimilar thereof), polysorbate 80, mannitol, and water for injection. In one embodiment, the formulation contains 80 mg of adalimumab, water for injection, 42 mg/ml of mannitol, and 1 mg/ml of polysorbate 80. An important aspect of the formulations and methods of the invention is the omission of a buffer and salt. Thus, in one embodiment, the formulations and methods of the invention do not contain any buffer(s) (e.g., citrate and phosphate) or salts.

The formulations disclosed in Fraunhofer 2012 are described as offering the advantage of reduced pain associated with injection in a patient by at least about 50% or more when compared to injecting adalimumab in any of the above-described formulations comprising at least one salt and/or at least one buffer.

The pharmaceutical formulations disclosed in Fraunhofer 2012 are also described as providing adalimumab formulations that surprisingly have improved bioavailability. The disclosed formulations in Fraunhofer 2012 are described as being based, at least in part, on the combination of only one or two excipients, i.e., a surfactant and a polyol or, alternatively, a surfactant alone. As described in the working examples included in Fraunhofer 2012, a formulation containing more than 50 mg/ml of adalimumab, and a polysorbate was shown to have increased bioavailability relative to other high concentration formulations, including the commercial adalimumab formulation described in the '583 patent which comprises adalimumab, sodium chloride, monobasic sodium phosphate dihydrate, dibasic sodium phosphate dihydrate, sodium citrate, citric acid monohydrate, mannitol, polysorbate 80, and water for injection. The increase in bioavailability is attributed to the combination of the antibody and the surfactant and the omission or removal of other excipients, including a buffer, polyol, and salt.

Cell Culture/Production

Biopharmaceutical antibodies such as ant-TNF antibodies are typically produced by culturing suitable host/vector systems to express the recombinant translation products of the DNAs encoding the same, which are then purified from culture media or cell extracts. Various mammalian cell culture systems are advantageously employed to fusion proteins and monocolonal antibodies because expression of recombinant proteins in mammalian cells because mammalian cell secretory pathways are known to facilitate the assembly and folding of biologically active proteins. [Could cite to Abbott Production IP]

In order to create soluble, secreted antibodies, that are released into the cell culture supernatant, either the natural signal peptide of the therapeutic moiety of the Fc-fusion protein is used, or preferably a heterologous signal peptide, i.e., a signal peptide derived from another secreted protein being efficient in the particular expression system used. If the antibody to be purified is expressed by mammalian cells secreting it, the starting material of the purification process of the invention is cell culture supernatant, also called harvest or crude harvest. If the host cells are cultured in a medium containing animal serum, the cell culture supernatant also contains serum proteins as impurities. Preferably, the antibody expressing and secreting cells are cultured under serum-free conditions. Alternatively, the anti-TNF antibody may also be produced in a chemically defined medium. Typically, the starting material of the purification process of the invention is serum-free cell culture supernatant that mainly contains host cell proteins as impurities.

In accordance with the present invention, the anti-TNF antibody can be produced in eukaryotic expression systems, including mammalian cells and glycoengineered yeast cells, resulting in glycosylated antibodies having a humanized profile of glycans. Glycosylation is one of the most common posttranslational modifications that occur during the production of a recombinant Fc-fusion protein using mammalian cell lines. Glycosylation can affect protein activity, solubility, stability and immunogenicity. Glycosylated proteins, such as monoclonal antibodies and Fc-containing fusion proteins are complex molecules and even a well-controlled product can consist of several hundred or more glycoforms characterized by having the same amino acid sequence but distinct glycan profiles (*Nature Biotechnology* 29(4):310 (2011)). Different glycoforms frequently have different physical and chemical properties.

The most common site of glycosylation in antibodies is through N-linkage of the Asn 297 side chain on the CH2 domain of the immunoglobulin heavy chain. The presence of oligosaccharides at the CH2 N-glycosylation site is known to affect the pharmacological and biological properties of Fc-containing proteins. The final glycan profile of a biopharmaceutical glycoprotein is influenced by the production host cell, the culture conditions and the purification processes used to manufacture the product.

In practice, CHO cell lines are typically the production cell line of choice because they offer well-characterized, selectable and amplifiable gene expression systems which facilitate high level recombinant protein expression in these cells (Kaufman, R. J., *Meth. Enzymol.* 185:527-566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

However, as expression systems and vectors have been improved to maximize levels of expression from eukaryotic hosts, not all of the recombinant protein expressed and secreted from these hosts is in the desired, most active conformation. Generally speaking, the desired conformation for a recombinant protein is the three-dimensional structure of a protein that most closely resembles, and/or duplicates the function of, the naturally occurring domain of that protein.

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual.* 3$^{rd}$ ed. Cold Spring Harbor Laboratory Press: Cold Spring Harbor, New York; Ausubel et al. eds. (2005) *Current Protocols in Molecular Biology*. John Wiley and Sons, Inc.: Hoboken, N.J.; Bonifacino et al. eds. (2005) *Current Protocols in Cell Biology*. John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.; *Nucleic Acid Hybridization*, Hames & Higgins eds. (1985); *Transcription And Translation*, Hames & Higgins, eds. (1984); *Animal Cell Culture* Freshney, ed. (1986); *Immobilized Cells And Enzymes*, IRL Press (1986); Perbal, *A Practical Guide To Molecular Cloning* (1984); and Harlow and Lane. *Antibodies: A Laboratory Manual* (Cold Spring Harbor Laboratory Press: 1988).

Manufacturing

The commercial manufacturing process for adalimumab comprises several chromatography steps, as well as a low pH treatment step and nanofiltration for virus inactivation/removal (EMEA European Public Assessment Report (EPAR), Scientific Discussion, published Mar. 30, 2006). Physico-chemical studies reveal that adalimumab is present in three major forms, corresponding to molecules carrying two, one or no C-terminal lysine. These three main molecular forms have been estimated to constitute about 85% of an adalimumab bulk preparation. The rest, representing approximately 15% of the bulk preparation, typically elutes as a number of poorly resolved peaks in an ion exchange HPLC assay. Despite extensive characterization of the more acidic species present in the three major forms of the adalimumab, no correlation between the shift and mobility and changes in antibody structure have been established by the innovator/originator. The EMEA concluded that because the species could not be resolved by traditional analytical methods (e.g., SDS PAGE), and their presence were demonstrated to not influence TNF-α binding in an in vitro model systems it was likely that the structural differences are minor. The EMEA further concluded that the fermentation step is likely critical for the formation of the acidic species, and the agency has indicated that a combination of in-process fermentation controls and weak cation exchange (WCX) chromatography for quantification constitutes an acceptable means of monitoring the presence of the more acidic molecular species for release specifications and for defining the stability of the product. (EMEA European Public Assessment Report (EPAR), Scientific Discussion, Published Mar. 30, 2006).

Regulatory authorities assume that each therapeutic protein has a unique and specific set of structural features (e.g., amino acid sequences, glycosylation profile, and folding) that are essential to their intended effect, and that even slight modifications can affect their immunogenicity and/or clinical efficacy. Therefore, it is not surprising that changes in manufacturing process used to produce an approved biopharmaceutical are tightly regulated by health authorities. When the manufacturer of a biopharmaceutical product changes its manufacturing process regulatory agencies will require the manufacturer to perform a comparability exercise comparing the quality of products produced using the pre- and post-change manufacturing processes. The exercise will usually include data collected from both physiochemical and functional assays.

The principles of the comparability exercise are established in guidelines such as the International Conference on Harmonization (ICH) Q5E which indicates that "the demonstration of comparability does not necessarily mean that the quality attributes of the pre-change and post-change product are identical, but that they are highly similar and that the existing knowledge is sufficiently predictive to ensure that any differences in quality attributes have no adverse impact upon safety or efficacy" (*Nature Biotechnology*, 29(4):310 (2011)). Generally speaking, health authorities and companies tolerate some degree of drift in a manufacturing process, provided that it does not alter the safety or efficacy of the product.

The commercial manufacturing process for adalimumab comprises several chromatography steps, as well as a low pH treatment step and nanofiltration for virus inactivation/removal (EMEA European Public Assessment Report (EPAR), Scientific Discussion, published Mar. 30, 2006). Physico-chemical studies reveal that adalimumab is present in three major forms, corresponding to molecules carrying two, one or no C-terminal lysine. These three main molecular forms have been estimated to constitute about 85% of an adalimumab bulk preparation. The rest, representing approximately 15% of the bulk preparation, typically elutes as a number of poorly resolved peaks in an ion exchange HPLC assay. Despite extensive characterization of the more acidic species present in the three major forms of the adalimumab, no correlation between the shift and mobility and changes in antibody structure have been established by the innovator/originator.

The EMEA concluded that because the species could not be resolved by traditional analytical methods (e.g. SDS PAGE), and their presence were demonstrated to not influence TNF-α binding in in vitro model systems it was likely that the structural differences are minor. The EMEA further concluded that the fermentation step is critical for the formation of the acidic species, and indicated that a combination of in-process fermentation controls and weak cation exchange (WCX) chromatography into regions for quantification constitutes an acceptable means of monitoring the presence of the more acidic molecular species for release specifications and for defining the stability of the product. (EMEA European Public Assessment Report (EPAR), Scientific Discussion, Published Mar. 30, 2006).

Chemical and/or charge heterogeneity involves a modification of the primary sequence of an antibody. Common alterations which can occur during the manufacture of a biological drug substance include changes to the disulfide bonds, modifications in N-glycosylation, C-terminal lysine processing, glycosylation of Lys residues, deamidation, isomerization, oxidation, and hydrolysis/fragmentation. Oxidative attack on proteins results in site-specific amino acid modifications, fragmentation of the peptide chain, aggregation of cross-linked reaction products, disulfide bond reshuffling (leading to misfolding), altered electrical charge and increased susceptibility to proteolysis. The amino acids in a peptide differ in their susceptibility to attack, and the various forms of activated oxygen differ in their potential reactivity. Primary, secondary, and tertiary protein structures alter the relative susceptibility of certain amino acids. Activated oxygen can abstract an H atom from cysteine residues to form a thiyl radical that will cross-link to a second thiyl radical to form disulphide bridges. Alternatively, oxygen can add to a methionine residue to form methionine sulphoxide derivatives.

Conformational heterogeneity relates to the distribution of the conformational states as defined by the intrinsic thermodynamic stability of a mAb under a given solution condition (Sharma, V., "The Formulation and Delivery of Monoclonal Antibodies", *Therapeutic Monoclonal Antibodies*, John Wiley & Sons (2009)). Typically a protein's native conformation is defined as the one that is prevalent under physiological conditions. Altered non-native conformations may be produced during the cell culture process as a result of misfolding, or may occur under different solution conditions ('557 patent). The non-native variants may be characterized by a different stability profile (i.e., more or less prone to aggregation or fragmentation), or be less biologically active. In practice, spectroscopic techniques, such as circular dichroism spectroscopy, differential scanning calorimetry and fluorescence spectroscopy can be used to determine the conformational heterogeneity of a protein composition which provides insight into the conformational stability of the composition.

Determining the conformation of a protein, and the relative proportions of a conformation of a protein in a mixture, can be done using any of a variety of analytical and/or qualitative techniques. If the two conformations resolve differently during chromatography, electrophoresis, filtering or other purification technique, then the relative proportion of a conformation in the mixture can be determined using such purification techniques. For example, in the non-limiting embodiments described below, at least two different conformations of an anti-TNF antibody can be resolved by way of hydrophobic interaction chromatography. Further, since far-UV Circular Dichroism has been used to estimate secondary structure composition of proteins (Perczel, et al., *Protein Engrg.* 4:669-679 (1991)), such a technique can determine whether alternative conformations of a protein are present. Still another technique used to determine conformation is fluorescence spectroscopy which can be employed to ascertain complimentary differences in tertiary structure assignable to tryptophan and tyrosine fluorescence. Other techniques that can be used to determine differences in conformation and, hence, the relative proportions of a conformation, are on-line SEC to measure aggregation status, differential scanning calorimetry to measure melting transitions (Tm's) and component enthalpies, and chaotrope unfolding.

Size heterogeneity can be primarily attributed to fragmentation and aggregation. Protein aggregation is a common problem in bioprocessing and can occur during expression, purification or storage. Aggregation is a particular challenge in downstream processes designed for the purification of proteins comprising Fc-regions which contain high levels of high molecular weight species; and is dependent on experimental variables such as, the amino acid sequence of the protein, the complexity of the protein, temperature, pH, and the type of ion present in a buffer and the buffer's ionic strength. Aggregation inhibitors reduce a polypeptide's tendency to associate in inappropriate or unwanted ternary or quaternary complexes.

Aggregation is a general term that encompasses several types of interactions or characteristics. Usually aggregation results from intermolecular associations of partially denatured protein chains, however, it may also result from chemical degradation and subsequent exposure of hydrophobic surfaces or from disulfide bond scrambling. Protein aggregates can arise from several mechanisms and may be classified in numerous ways, including soluble/insoluble, covalent/noncovalent, reversible/irreversible, and native/denatured. Because the term "aggregate" encompasses heterogeneous species ranging from soluble dimers to visible particles comprising millions of monomers, it is difficult to exactly measure, characterize and quantify. In addition, although there are clear guidelines regarding the number of particles ≥10 μm and ≥25 μm in size that may be present in a pharmaceutical composition, the level of soluble aggregates (i.e., dimers and trimers which are not visible as discrete particles and which are not removed by a filter with a pore size of 0.22 μm) that are acceptable are not well defined.

Aggregation is one of the major challenges encountered during the development of a manufacturing process for an Fc-fusion protein. Throughout production, the protein solution is pumped, stirred, and filtered and encounters numerous containers made of different materials. All of these factors can potentially promote the formation of aggregates. For example, during cell culture, the protein is secreted from the cell into culture medium containing the cells, ions, nutrients for the cells, host cell proteins (including proteases), dissolved oxygen, and other species. The resulting cell culture fluid is harvested and purified over a variety of chromatography resins (e.g., protein A, and anion or cation exchange resins) which may involve the use of acidic, or high pH and/or high ionic strength elution buffers. Finally, the protein is formulated using ultrafiltration/diafiltration. The formulated protein may be stored frozen for some period of time before being filled into its final container.

The accumulation of high levels of protein during cell culture can promote intracellular aggregation attributed to either the interactions of unfolded protein molecules or to inefficient recognition of the nascent polypeptide chain by molecular chaperones required for proper folding. In addition, secretion of the biopharmaceutical protein into the cell culture media exposes the protein to unfavorable conditions. However, it is possible to influence the amount of aggregates produced during the upstream unit operations required to manufacture a biopharmaceutical protein by carefully selecting the expression system and cell culture conditions. For example, the culture temperature can be shifted during the production phase, or components can be added to the growth or feed media to influence the ability of the expressed protein to fold into a native structure.

Because association between two or more antibody molecules is a prerequisite for aggregation, the process is often concentration dependent. Depending upon the mechanism driving the association, a variety of aggregates may be formed. Some aggregates are formed due to a tendency for self-association, which is concentration dependent process that can be reversible upon dilution. Fc-containing proteins, including mAbs, can form covalent irreversible aggregates through intermolecular disulfide cross-links. In CHO cells, disulfide bonds formation occurs after the nascent polypeptide is translocated to the lumen of the endoplasmic reticulum (ER). Formation of disulfide bonds typically require an oxidative environment. In the absence of this environment, free thiols on the cysteines may remain unpaired, leading to improper folding.

Aggregation, or size heterogeneity, can alter not only the therapeutic, pharmacokinetic and pharmacodynamics profiles of the therapeutic protein, but also has a negative impact on the safety profile, because it is considered a strong risk factor for immunogenicity. Therefore, it is well established that aggregation of biopharmaceutical proteins is undesirable as it may result in immunogenicity (Cleland, et al., *Crit. Rev. Therapeutic Drug Carrier Systems,* 10:307 (1993)). Aggregation of proteins may either reveal new epitopes or leads to the formation of multivalent epitopes, which may stimulate the immune system. Factors, which could be considered to contribute to aggregate formation, include formulation, purification processes, viral inactivation procedures and storage conditions of intermediates and finished product. For protein therapeutics, the presence of aggregates of any type is typically considered to be undesirable because of the concern that the aggregates may lead to an immunogenic reaction (small aggregates) or may cause adverse events on administration (particulates) (Cromwell, M. E., et al., *Protein Aggregation and Bioprocessing, AAPS Journal.* 8(3): E572 (2006)).

Chemical degradation represents one of the major degradation pathways of Fc-containing proteins. It is well known that chemical degradation pathways often exhibit a pH dependence. For example, solution environments of higher than pH 7.0 can promote protein deamidation of the asparagine residues, disulfide exchange and aggregation, while lower pH values (e.g., pH 4.0 and below) can promote isomerization, hydrolysis and fragmentation. In addition, because pH can have an impact on the tertiary conformation and net charge of a protein, physical aggregation can also exhibit a pH dependence.

During the manufacture of biologics, a protein molecule is subjected to physical stress, such as high temperature, multiple chromatography steps, ultracentrifugation, pumping, and stirring to name some examples. It also goes through chemical stress from exposure to salts, buffers, acids, and bases.

Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation.

The pharmaceutical formulations of the present invention preferably exhibit degradation (e.g., fragmentation, aggregation or unfolding) of not more than about 5% over a period of 2 years when stored at refrigerated conditions of 2-8° C.

It is well known that many aspects of biopharmaceutical production and formulation are pH sensitive. Maintaining the correct pH of a finished biopharmaceutical product is required to ensure the stability, effectiveness and shelf-life of the active agent. In general, currently marketed biopharmaceuticals are formulated in the pH range of 5.0 to 8.0. When the pH of the pharmaceutical composition is set at or near physiological levels comfort of the patient upon administration is maximized. There are multiple formulation aspects (e.g., osmolality, buffering capacity, excipients etc.) that contribute into perceived sensation of irritation, itching, burning, stinging during product administration/self-administration.

In order to maintain pH, one or more buffering agents are incorporated into pharmaceutical product. A variety of buffering agents are available for pharmaceutical use. Selection of a suitable buffer requires a consideration of its buffering capacity, the solubility of the biopharmaceutical in the buffer and the desired pH of the formulation. The buffer should be stable and effective at maintaining pH over the range of conditions to which it will be exposed during formulation and storage of the product. It should not be deleteriously affected by oxidation or other reactions which could occur during the upstream or downstream unit operations required for the production and purification of the biopharmaceutical drug substance.

In practice, liquid formulation development results from a series of steps which require selection of an appropriate solution pH and of excipients selected to minimize degradation and promote stability of individual therapeutic agent. The choice of a formulation buffer species and molarity is one of the most significant aspects of the formulation development process. Selection of the buffer system and concentration is based on the buffer capacity required to stabilize the biopharmaceutical agent under the conditions to which the product will be exposed.

The pharmaceutical compositions of the invention comprise a buffer which functions, in part, to maintain the pH of the composition in a desired range. Numerous buffering agents are well know to those of skill in the art are known to be suitable for use in protein formulations are well known. Each of them works over a relatively narrow range of pH. Several factors need to be considered when choosing a buffer. For example, the buffer species and its concentration need to be defined based on its pKa and the desired formulation pH. Equally important is to ensure that the buffer is compatible with the protein drug, and any excipients that are present in the formulation. It is also important in pharmaceutical compositions to consider the possibility that a given buffering agent will be unacceptable for administration for ancillary reasons, such as deleterious effects on patient comfort. Some buffering agents are unsuitable for this purpose because they cause stinging or irritation at the point of administration. For example, citrate is known to cause stinging upon injection. Such effects are more pronounced for SC and IM administration, because the formulation remains at the administration site for some time, than for IV administration, where the formulation is diluted immediately.

Typical buffers used for biopharmaceuticals formulations include sodium or potassium salts of acetic, citric, gluconic, glutamic, phosphoric, succinic and other organic acids or histidine and the corresponding acids. Phospate buffers (e.g., phosphate or phosphate-succinate) are suitable for use in formulating a biosimilar adalimumab. As disclosed herein, one buffer suitable for use in formulating a biosimilar anti-TNF monoclonal is a phosphate buffer having buffering capacity at or near about pH 5.1 to about 5.6. Alternatively, a buffer comprising a dual buffering system, for example a phosphate-succinate buffer, having a buffering capacity at or near about pH 5.1 to about a pH of 5.6 can be used to prepare the pharmaceutical compositions of the invention.

In various embodiments, an aqueous formulation can be prepared having a phosphate or phosphate-succinate buffer with a desired pH between about 5.3 and 5.5, sodium chloride, a stabilizer selected from trehalose, mannitol, xylitol or sorbitol, Polysorbate 80 and an effective amount of a biosimilar form of adalimumab.

The phosphate component of a phosphate-succinate formulation can be supplied to the buffering system in a variety of different forms. For example, the phosphate component can be supplied as sodium phosphate, or potassium phosphate. It can be prepared with the acid form, monobasic form, dibasic form, or any combination thereof.

Phosphate buffer was prepared by sequential dissolution of calculated amounts of Sodium Phosphate, Monobasic, Monohydrate and Sodium Phosphate Dibasic, Heptahydrate. In another embodiment Phosphate buffer of desired concentration can be obtained by titration of Phosphoric acid solution of target concentration with sodium hydroxide solution until desired pH is obtained. The phosphate buffer can be prepared via stock solution with further dilution to the final buffer concentration and the target pH can be additionally controlled via addition of sodium hydroxide or phosphoric acid if necessary.

Phosphate-succinate buffer was prepared by sequential dissolution of calculated amounts of Sodium Phosphate, Dibasic, Heptahydrate and Succinic acid. In another embodiment stock solution of Sodium Phosphate can be titrated with 0.1M solution of succinic acid solution of target succinate concentration until desired pH is obtained. The phosphate-succinate buffer can be prepared via stock solution with further dilution to the final buffer concentration and the target pH can be additionally controlled via addition of sodium hydroxide or succinic acid if necessary.

In a particular embodiment, the invention provides a stabilized liquid formulation containing a biosimilar form of adalimumab at about 40 mg/mL or about 50 mg/mL, at about pH 5.3, at about pH 5.6 or about pH 5.4.

In various embodiments, a phosphate buffer system having sufficient buffering capacity to maintain a target pH of about 5.0 to about 5.7 at a selected temperature can be use to prepare the formulations of the invention. Useful concentrations of sodium phosphate can be between about 5 to about 100 mM, between about 10 to about 75 mM, between about 10 to about 50 mM, between about 10 to about 30 mM. In various other embodiments, the sodium phosphate concentration can be about 5 mM, 10 mM, 15 mM, 20 mM, 25 mM, 30 mM, 35 mM, 40 mM, 45 mM, 50 mM. Other concentrations of sodium phosphate can be appropriate provided that the buffer has sufficient buffering capacity to maintain the desired target pH, at a selected storage temperature.

In various embodiments, the phosphate-succinate buffered pharmaceutical formulation comprises of sodium phosphate between about 6 to about 50 mM, and succinate between about 4 to about 50 mM, between about 5 to about 50 mM, between about 10 to about 30 mM. In various other embodiments, the sodium phosphate concentration can be about 6 mM, 12 mM, 18 mM, 24 mM, 30 mM, 36 mM, 42 mM, 48 mM, 54 mM, 60 mM while the succinic acid is 4 mM, 8 mM, 12 mM, 16 mM, 20 mM, 24 mM, 28 mM, 32 mM, 36 mM, 40 mM, correspondingly. The ratio between phosphate and succinate is 3 to 2, correspondingly. Other concentrations of sodium phosphate and succinic acid can be appropriate provided that the composition has sufficient buffering capacity to maintain the desired target pH, at a selected storage temperature. In alternative embodiments, the sodium chloride concentration can range from about 50 mM to about 130 mM. For example, the sodium chloride concentration can range from about 70 to about 110 mM. In particular embodiments, the sodium chloride concentration can be about 75 mM, about 80 mM, about 85 mM, about 90 mM, about 95 mM, about 100 mM, about 105 mM, or about 110 mM.

In one embodiment, an aqueous formulation can be prepared having a phosphate buffer species with a desired pH, sodium chloride, a stabilizer, a surfactant and an effective amount of a biosimilar adalimumab antibody. In an alternative embodiment, an aqueous formulation can be prepared having a phosphate-succinate buffer with a desired pH, sodium chloride, a stabilizer, a surfactant and an effective amount of a biosimilar adalimumab antibody.

Selection of a target solution pH for the biopharmaceutical composition is a critical parameter that is often the first step performed during the development of a liquid biopharmaceutical formulation. Since individual biopharmaceutical proteins are characterized by different amino acid sequences and different isoelectric points (pI values), the optimal pH for a particular monoclonal antibody or fusion protein will differ based on the particular balance between various degradation processes. To ensure adequate solubility of a protein, the formulation pH should be at least 0.5 units below or above its pI.

The structure of water surrounding a folded protein in an aqueous formulation is a critical for maintaining the structure of the protein and excipients are often added to stabilize this interaction. Amino acids and sugars are commonly included in formulations in order to mediate a type of hydration effect. In the presence of a stabilizing excipient, a protein may preferentially hydrate which will have the effect of excluding the excipient, which will cause more water molecules to be found on the surface of the protein than in the bulk, which functions to stabilize the protein Jorgensen, L., *Expert Opin. Drug Deliv.* 6:11 (2009). Stabilization by this type of a hydration effect might be attributed to the prevention of the direct interaction between proteins which if left unchecked can promote protein aggregation.

Excipients

Formulations in accordance with various aspects and embodiments of the invention may contain, among others, excipients which inhibit adsorption, prevent oxidation, maintain pH, stabilize the biopharmaceutical protein and control the osmolality of the pharmaceutical composition. In general, excipients can be chosen on the basis of the mechanisms by which they stabilize proteins against various chemical and physical stresses that could occur during a manufacturing process, under particular storage conditions, or associated with a particular mode of administration. In addition, an excipient can function as a diluent or employed to reduce the viscosity in high protein formulations in order to enable the delivery and/or enhance patient convenience.

The concentration or amount of an excipient to use in a formulation will vary depending on, for example, the amount of the active biopharmaceutical protein included in the formulation, the amount of other excipients included in the desired formulation, whether a diluent is needed, the amount or volume of other components in the formulation, and the desired tonicity or osmolality that is desired to be achieved. In various embodiments, different types of excipients can be combined in a single formulation. Accordingly, a single formulation can contain a singe excipient, two, three or more different types of excipients. Given the teachings and guidance provided herein, those skilled in the art can determine what amount or range of excipient can be included in a suitable formulation of the invention to achieve a formulation that promotes the retention of anti-TNFα antibody stability.

The use of excipients in liquid formulations is an established practice to stabilize proteins against degradation or aggregation processes attributed for instance, to stresses that occur during manufacturing, shipping, storage, pre-use preparation, or administration. In practice, the presence of a particular excipient in a formulation may have more than one effect or purpose.

A variety of publications and reviews are available on protein stabilization and formulation excipients useful in this regard, such as Arakawa, et al., "Solvent interactions in pharmaceutical formulations," *Pharm. Res.* 8(3):285-91 (1991); Kendrick, et al., "Physical stabilization of proteins in aqueous solution," in: RATIONAL DESIGN OF STABLE PROTEIN FORMULATIONS: THEORY AND PRACTICE, Carpenter and Manning, eds. *Pharmaceutical Biotechnology* 13:61-84 (2002), and Randolph, et al., "Surfactant-protein interactions," *Pharmaceutical Biotechnology* 13:159-75 (2002), each of which is herein incorporated by reference in its entirety, particularly in parts pertinent to excipients for formulations in accordance with the current invention, especially as to protein pharmaceutical products for veterinary and/or human medical uses.

The choice of excipients is often based on previous experience, this will be particularly true with regards to the formulation of biosimilar proteins, which will have to established to the satisfaction of regulatory authorities that a particular biosimilar formulation is "highly similar" to the reference product. For an excipient to be approved as part of a formulation approved for human use its inclusion has to be justified, the compatibility with the active ingredient established, and the quality (or grade) will have to shown to fulfill the requirements for the final product. The FDA has made a database and an "Inactive Ingredients Guide" from 1996 publicly available. The Inactive Ingredients Database provides information on inactive ingredients present in FDA-approved drug products. This information can be used by industry as an aid in developing drug products. For new drug development purposes, once an inactive ingredient has appeared in an approved drug product for a particular route of administration, the inactive ingredient is not considered new and may require a less extensive review the next time it is included in a new drug product. For example, if a particular inactive ingredient has been approved in a certain dosage form at a certain potency, a manufacturer could consider it safe for use in a similar manner for a similar type of product.

The optimum solubility of a biopharmaceutical protein is attributed to a combination of several parameters including, but not limited to, ionic strength, pH and solution composition, and a minimum solubility is often observed around the protein's pI value.

The osmolality of a pharmaceutical composition is preferably regulated in order to maximize the active ingredient's stability and also to minimize discomfort to the patient upon administration. A tonicity modifier is understood to be a molecule that contributes to the osmolality of a solution. Non-ionic and ionic agents may be used to adjust the osmolality (tonicity) of compositions in accordance with the invention, including many well known and other lesser known compounds useful for this purpose. Salts are useful in this regard, for instance. In embodiments, NaCl is used as a tonicifying agent. In embodiments KCl, MgCl2, CaCl2 or another salt is used as a tonicifying agent, alone or in combination with other tonicifying agents.

Salts may be used in accordance with embodiments of the invention to, for example, adjust the ionic strength and/or the isotonicity of a formulation and/or to improve the physical stability of a protein or other ingredient(s) of a composition. In embodiments salts prevent or reduce protein insolubility and/or aggregation. In embodiments salts also are effective for reducing the viscosity of protein formulations.

Polyols include sugars, e.g., mannitol, sucrose, trehalose and sorbitol and polyhydric alcohols such as, for instance, glycerol and propylene glycol. Generally, polyols are kosmotropic. Polyols are useful stabilizing agents in liquid and formulations to protect proteins from physical and chemical degradation processes, and can function to adjust the tonicity of formulations.

Tonicity agents and/or stabilizers included in a liquid formulation can be used, for example, to achieve a physiologic osmolality (e.g., isotonicity), of a formulation that is suitable for human or animal administration, or to facilitate the maintenance of a biopharmaceutical's structure, and/or to minimize electrostatic, solution protein-protein interactions. Examples of tonicity agents and/or stabilizers include polyols, salts and/or amino acids.

Aggregation inhibitors are added to pharmaceutical compositions to reduce a biopharmaceutical's tendency to associate in inappropriate or unwanted ternary or quaternary complexes.

Proteins in pharmaceutical compositions are susceptible to adsorption on surfaces and to denaturation and consequent aggregation at air-liquid, solid-liquid, and liquid-liquid interfaces. These effects generally scale inversely with protein concentration, and typically are exacerbated by physical agitation, such as that generated during the shipping and handling of a product. In practice, surfactants are commonly used to maintain protein conformational stability thereby minimizing, reducing or preventing surface adsorption. The use of surfactants in this regard is protein-specific, since any given surfactant typically will stabilize some proteins and destabilize others. Suitable surfactants for use in the invention in this regard include polysorbate 20, polysorbate 80, other fatty acid esters of sorbitan polyethoxylates, and poloxamer 188.

Filtration membranes are used throughout the purification process to remove impurities, to perform buffer exchange, and to concentrate the protein. In practice, ultrafiltration/diafiltration (UF/DF) is typically performed to exchange the buffer and to increase the protein concentration in solution. During the UF unit operation, the concentration of the biopharmaceutical protein at that membrane surface can be much higher than that of the bulk solution. Locally high concentrations can promote the formation of aggregates. In addition, the mechanical stresses that accompany multiple passes through the pump during the UF/DF process can also promote aggregation.

A pharmaceutical formulation comprising of a biosimilar form of adalimumab, in one of the formulations of this invention is particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative.

A formulation of the invention can be administered, for example, with medical devices known in the art, such as pre-filled syringes and autoinjectors, such as, e.g., SureClick™, Injectease™, Genject™, injector pens such as GenPen™ or Physiolis™ and needleless devices such as MediJector™ and BioJector™. In addition, the present pharmaceutical composition can also be adapted for yet to be discovered administration methods. The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

Embodiments of the invention are not to be limited in scope by the specific embodiments described herein which are intended as illustrations of embodiments of the invention, and any compositions or methods which are functionally equivalent are within the scope of this invention. Various modifications of the invention in addition to those shown and described herein will become apparent to those skilled in the art form the foregoing description. Such modifications are intended to fall within the scope of the appended claims.

The specific embodiments described herein are offered by way of example only, and the invention is to be limited by the terms of the appended claims, along with the full scope of equivalents to which such claims are entitled.

EXAMPLES

Materials and Methods

Sample and formulations preparation steps were performed at Sterile Product Development, Merck Research Laboratories, Summit, N.J. Table 2 lists the excipients used for preformulation and formulation screenings. Buffer exchanges were carried out at 2-8° C. in 50 kDa Amicon® Ultra—15 centrifugal filter units, with sample to buffer volume ratio of 1:1, and three volume exchanges. mAb concentrations were determined by UV280 absorption.

TABLE 2

List of materials

| Name | Vendor |
|---|---|
| Polysorbate 80 | In house |
| Sucrose | Fisher |
| α,α-Trehalose Dihydrate | In house |
| D-Mannitol | Fisher |
| Xylitol | Sigma-Aldrich |
| D-Sorbitol | Sigma-Aldrich |
| Sodium Chloride | Fisher |
| Sodium Phosphate Dibasic Heptahydrate (Na2HPO4•7H2O) | Sigma Aldrich |
| Sodium Phosphate Monobasic Monohydrate (NaH2PO4•H2O) | Fisher |
| L-Histidine, 98% | Acros |
| Succinic Acid, 99% | Alfa-Aesar |
| Citric Acid Monohydrate | Fisher |
| Sodium Citrate | Fisher |
| Hydrochloric Acid, 1N | Fisher |
| Sodium Hydroxide, 1N | Fisher |

Opalescence

Opalescence was assessed by measuring the difference between optical densities (OD) at 350 nm and at 550 mn.

Size Exclusion Chromatography (HP-SEC)

Irreversible, soluble aggregates were quantitatively measured using Size Exclusion High Performance Liquid Chromatography (HP-SEC). Chromatography was conducted using a Waters 2695 Liquid Chromatography system and an Amersham Biosciences Superdex 200 HR 10/300 GL column. The data was analyzed using the Empower2 software package, based on relative % areas of main, aggregated and fragmented peaks.

Ion Exchange Chromatography (HP-IEX)

Acidic and basic charge variants were quantitatively measured using Ion Exchange High Performance Liquid Chromatography (HP-IEX). Chromatography was conducted using a Waters 2695 Liquid Chromatography system and a Dionex ProPac® WCX-10 2×250 mm column. The data was analyzed using the Empower2 software package. Relative % of total acidic and basic variants was calculated along with % contribution from the main peak.

Differential Scanning Calorimetry (DSC)

Differential scanning calorimetry (DSC) was performed with Microcal™ VP-DSC. Placebo was used in the reference cell. The data was processed by subtracting from each sample termogram, a corresponding placebo-placebo scan, fitting a baseline to the trace using the ORIGIN® software package, and determining the onset temperature of the first transition ($T_{onset}$° C.).

Dynamic Light Scattering (DLS)

The size and distribution of the mAb in different formulations was determined at 20° C. on Nano-ZS light scattering instrument (Malvern Instruments) using backscatter detection at 173°. A single exponential was fit to the correlation function (Cumulants analysis) to obtain the intensity weighted mean hydrodynamic diameter ($Z_{average}$) and the polydispersity index (PDI). Samples were prepared at 5 mg/mL. For each formulation, three separate measurements were made. Viscosity adjustments were made for each buffer and excipient system. The respective dispersant viscosities were measured using the MINIVIS II falling ball micro viscometer (Grabner Instruments).

Example 1

Preformulation Screening

Screening Design: Four (4) buffers, five (5) stabilizers and four (4) salt concentration levels were screened. The formulation compositions used preformulation screening is shown in Tables 3-5.

Formulations were prepared by mixing predetermined amounts of stabilizers, buffer species, salt concentrations and mAb. Polysorbate 80 was used as a surfactant. The pH across all formulations was 5.3±0.1. For all formulations, placebos were also prepared. The solutions were filtered using the Millipore Disposable Vacuum Filtration System with 0.22 µm PVDF Membrane. Screening was conducted in Type I glass vials that were stoppered and crimped.

TABLE 3

Composition of formulations for screening 4 buffer species

| | Buffer System | | | |
|---|---|---|---|---|
| Composition | Histidine | Phosphate | Succinate | Succinate/Phosphate* |
| mAb (mg/mL) | 50 | 50 | 50 | 50 |
| Buffer Concentration (mM) | 10 | 10 | 10 | 10 |
| Mannitol (% w/v) | 1.2 | 1.2 | 1.2 | 1.2 |
| NaCl Concentration (mM) | 105 | 105 | 105 | 105 |
| Polysorbate 80 (% w/v) | 0.1 | 0.1 | 0.1 | 0.1 |

*5 mM Succinate + 5 mM Phosphate Buffer

TABLE 4

Composition of formulations for screening stabilizers

| | Stabilizers | | | | | |
|---|---|---|---|---|---|---|
| Composition | Xylitol | Sorbitol | Mannitol | Sucrose | Trehalose | None |
| mAb (mg/mL) | 50 | 50 | 50 | 50 | 50 | 50 |
| Succinate Concentration (mM) | 10 | 10 | 10 | 10 | 10 | 10 |
| Stabilizer Concentration (% w/v) | 5 | 5 | 5 | 5 | 5 | 0 |
| NaCl Concentration (mM) | 105 | 105 | 105 | 105 | 105 | 105 |
| Polysorbate 80 (% w/v) | 0.1 | 0.1 | 0.1 | 0.1 | 0.1 | 0.1 |

* 5 mM Succinate + 5 mM Phosphate Buffer

TABLE 5

Composition of formulations for screening salt concentrations

| | NaCl Concentration (mM) | | | |
|---|---|---|---|---|
| Composition | 0 | 50 | 100 | 150 |
| mAb (mg/mL) | 50 | 50 | 50 | 50 |
| Succinate Concentration (mM) | 10 | 10 | 10 | 10 |
| Mannitol (% w/v) | 1.2 | 1.2 | 1.2 | 1.2 |
| NaCl Concentration (mM) | 0 | 50 | 100 | 150 |
| Polysorbate 80 (% w/v) | 0.1 | 0.1 | 0.1 | 0.1 |

* 5 mM Succinate + 5 mM Phosphate Buffer

Formulations were monitored over a period of 3, 6 and 10 weeks at 5° C. and 50° C. for signs of degradation. At each time point, formulations were subjected to detailed characterization tests, consisting of $UV_{280}$, MFI, Size Exclusion Chromatography (HP-SEC), Ion Exchange Chromatography (HP-IEX), Dynamic Light Scattering (DLS), Differential Scanning calorimetry (DSC) and Opalescence.

Results—Effect of Buffer Species At the end of stress exposure (10 weeks at 50° C.), succinate-based formulation demonstrated the least opalescence. The order of decreasing opalescence observed was succinate<phosphate<succinate+phosphate<histidine (FIG. 1A). However, based on the % acidic variants data, histidine was the most preferred species, followed by phosphate<succinate+phosphate<succinate (FIG. 1B).

Histidine was ruled out as the preferred buffer species based on the DSC thermograms generated (FIG. 2), which clearly demonstrate a conformational change in the histidine-based formulations.

Conclusion Based on the aforementioned data, phosphate and phosphate and succinate were selected as lead buffer species, formulations of which were further optimized using the DOE-based full factorial design.

Figure 3B:
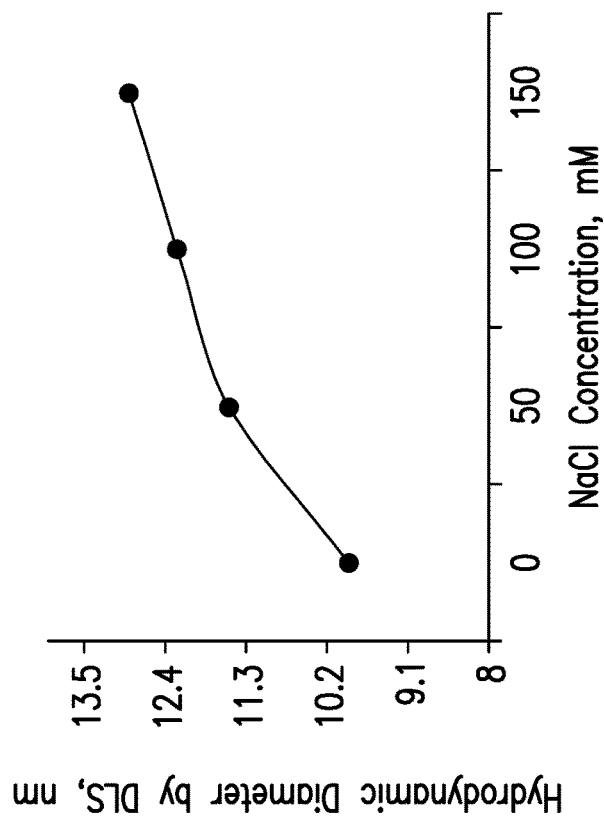
FIGS. 3A-3B provides graphic representation of the effect of salt on opalescence as estimated by a difference in absorption at 350 and 550 nm (FIG. 3A); and the effect of salt on hydrodynamic diameter (Zave) as measured by DLS (FIG. 3B).
Figure 3A:
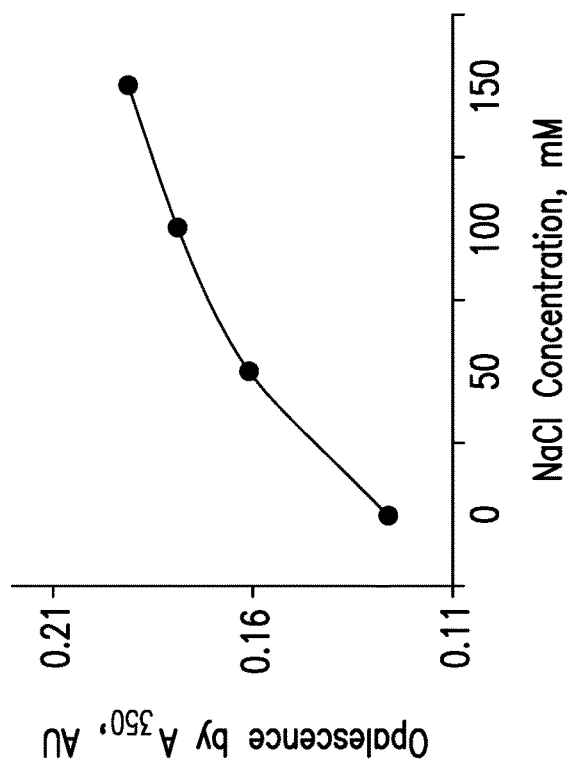

Results—Effect of Salt At the end of stress exposure (10 weeks at 50° C.), low salt formulations demonstrated the least opalescence (FIG. 3A). A similar trend was observed in the hydrodynamic diameter numbers ($Z_{ave}$) where the increase in NaCl concentration was associated with the increase in protein size (FIG. 3B). Overall, increasing sodium chloride concentrations was correlated with increased aggregation, particulate formation, opalescence and hydrodynamic diameter. However, improved biochemical stability was achieved in the presence of relatively higher levels of sodium chloride. Therefore, based on the % acidic variants and corresponding main peak HP-IEX data, high salt concentration was preferred (FIG. 4).

Figure 5B:
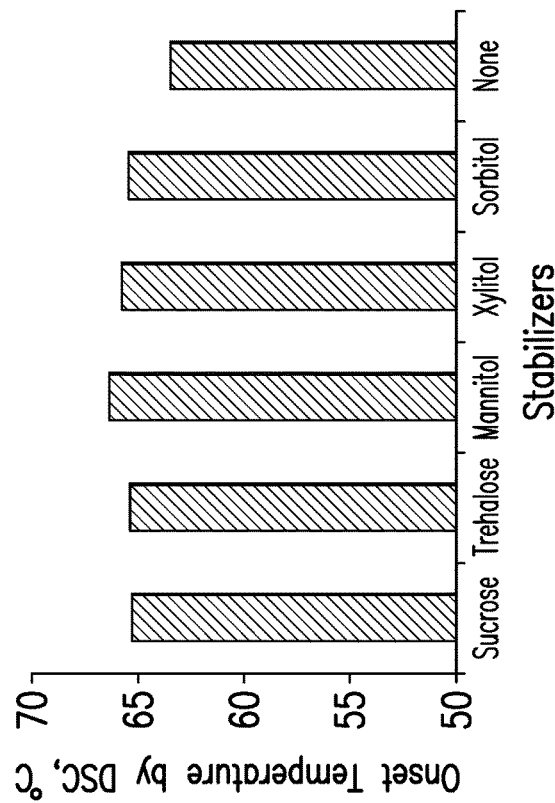
FIG. 5A-5B provides a graphic representation of the effect of stabilizer on % main peak (FIG. 5A) as measured by HP-IEX; and the effect of stabilizer the onset temperature (FIG. 5B) as measured by DSC.
Figure 5A:
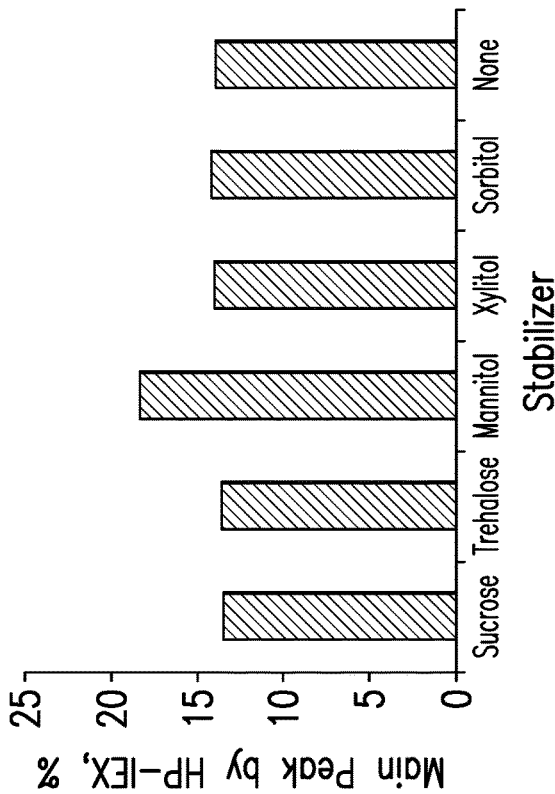
Figure 6:
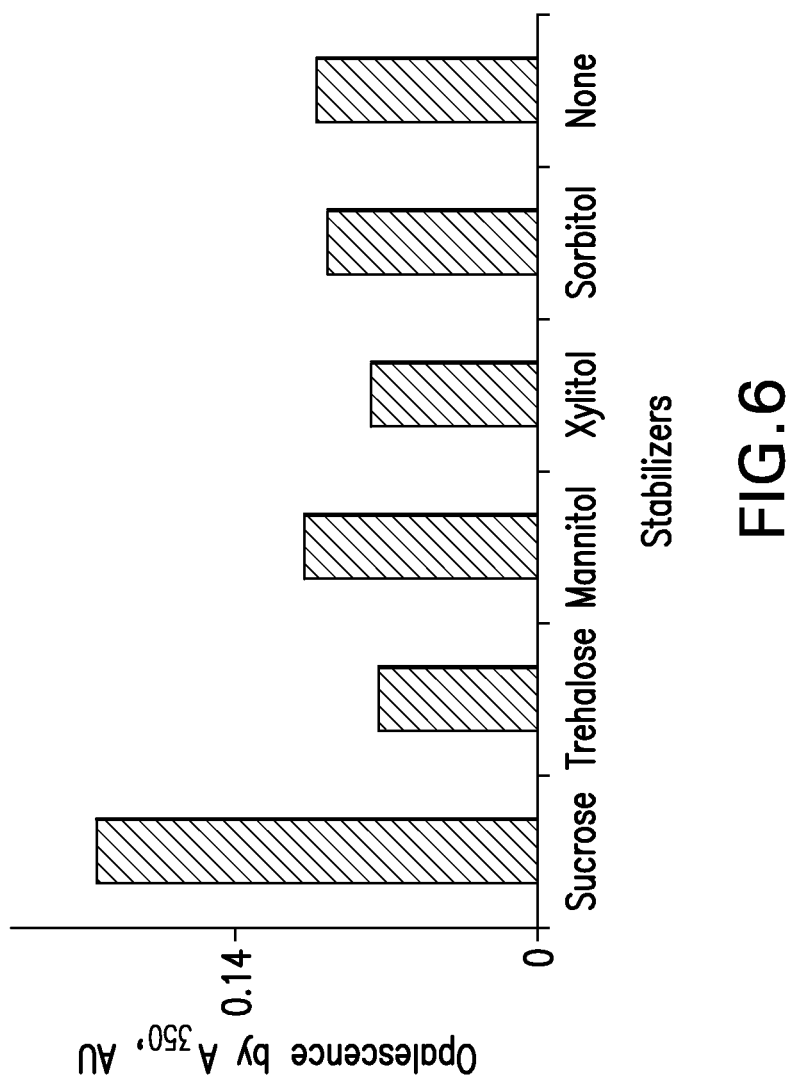
FIG. 6 provides a graphic representation of the effect of stabilizer on turbidity as estimated by a difference in absorption at 350 and 550 nm.

Although increasing concentrations of PS80 were observed to reduce opalescence and formation of particulates, the screening data established that it PS80 concentration had no significant impact in thermal stress studies.
Conclusion Based on the aforementioned data, the presence of salt was determined to be a critical for protein stability; and the concentration of salt was identified as a parameter that needed to be optimized.
Results—Effect of Stabilizer Generally speaking, in thermal stress studies polyols, trehalose and sucrose were superior stabilizers as compared to other disaccharides, cyclodextrins and glycosides.
At the end of stress exposure (10 weeks at 50° C.), based on the % main peak data from HP-IEX, amongst polyols, mannitol was the most preferred stabilizer (FIG. 5A). Amongst disaccharides, no significant difference between sucrose and trehalose was observed.
Based on the DSC thermograms generated (FIG. 5B), presence of a stabilizer did impart conformational stability to the protein. Again, mannitol was the preferred stabilizer with the highest onset temperature. No significant difference between sucrose and trehalose was observed.
Amongst disaccharides, the presence of sucrose led to increase in opalescence. Amongst polyols, xylitol-based formulations were the least opalescent (FIG. 6).
Conclusion Based on the aforementioned data, mannitol and trehalose were selected as lead stabilizer species, formulations of which were further optimized.

Example 2

Formulation Optimization

Study Design—Formulations were prepared by mixing predetermined amounts of stabilizers, buffer species, salt concentrations and biosimilar anti-TNF monoclonal antibody at 50 mg/mL. Polysorbate 80 was used as a surfactant. The pH across all formulations was 5.3±0.1. For all formulations, placebos were also prepared. The solutions were filtered using the Millipore Disposable Vacuum Filtration System with 0.22 μm PVDF Membrane. Originator formulation was manufactured and screened to facilitate a direct comparison with the studied formulations. Table 6 shows the list of formulations screened, identified by a reference number (#) and their respective compositions. The term "active" is used in Table 6 to refer to the concentration of anti-TNF antibody (e.g., adalimumab) that is present in each of the formulations. The formulations were filled in both vials and pre-filled syringes. Formulations were monitored over a period of 1, 3 and 6 months at 5, 25 and 40° C. for signs of degradation. At each time point, formulations were subjected to detailed characterization tests, consisting of UV280, MFI, Size Exclusion Chromatography (HP-SEC), Ion Exchange Chromatography (HP-IEX), Dynamic Light Scattering (DLS), Differential Scanning calorimetry (DSC) and Opalescence.
Results—Effect of buffer and stabilizer species, sodium chloride concentration, were studied for 6 months at 5, 25 and 40° C. Overall, acidic variants decreased with increase in salt concentration, and in presence of phosphate buffer species. No significant difference between trehalose and mannitol was observed.

TABLE 6

| # | Formulation |
|---|---|
| 02 | 50.00 mg/mL active; 4.165 mg/mL NaCl; 54.0 mg/mL trehalose 2H$_2$O; 1 mg/mL PS80; 1.52 mg/mL mono basic Na phosphate 2H$_2$O; 0.05 mg/mL dibasic Na phosphate 2H$_2$O; pH 5.3 ± 0.1 |
| 03 | 50.00 mg/mL active; 4.165 mg/mL NaCl; 26.0 mg/mL mannitol; 1 mg/mL PS80; 1.52 mg/mL mono basic Na phosphate 2H$_2$O; 0.05 mg/mL dibasic Na phosphate 2H$_2$O; pH 5.3 ± 0.1 |
| 04 | 50.00 mg/mL active; 4.165 mg/mL NaCl; 54.0 mg/mL trehalose 2H$_2$O; 1 mg/mL PS80; 1.07 mg/mL dibasic Na phosphate 2H$_2$O; 0.48 mg/mL succinic acid; pH 5.3 ± 0.1 |
| 05 | 50.00 mg/mL active; 4.165 mg/mL NaCl; 26.0 mg/mL mannitol; 1 mg/mL PS80; 1.07 mg/mL dibasic Na phosphate 2H$_2$O; 0.48 mg/mL succinic acid; pH 5.3 ± 0.1 |
| 06 | 50.00 mg/mL active; 6.165 mg/mL NaCl; 27.0 mg/mL trehalose 2H$_2$O; 1 mg/mL PS80; 1.52 mg/mL mono basic Na phosphate 2H$_2$O; 0.05 mg/mL dibasic Na phosphate 2H$_2$O; pH 5.3 ± 0.1 |
| 07 | 50.00 mg/mL active; 6.165 mg/mL NaCl; 13.0 mg/mL mannitol; 1 mg/mL PS80; 1.52 mg/mL mono basic Na phosphate 2H$_2$O; 0.05 mg/mL dibasic Na phosphate 2H$_2$O; pH 5.3 ± 0.1 |
| 08 | 50.00 mg/mL active; 6.165 mg/mL NaCl; 27.0 mg/mL trehalose 2H$_2$O; 1 mg/mL PS80; 1.07 mg/mL dibasic Na phosphate 2H$_2$O; 0.48 mg/mL succinic acid; pH 5.3 ± 0.1 |
| 09 | 50.00 mg/mL active; 6.165 mg/mL NaCl; 13.0 mg/mL mannitol; 1 mg/mL PS80; 1.07 mg/mL dibasic Na phosphate 2H$_2$O; 0.48 mg/mL succinic acid; pH 5.3 ± 0.1 |
| 10 | 50.00 mg/mL active; 5.165 mg/mL NaCl; 40.5 mg/mL trehalose 2H$_2$O; 1 mg/mL PS80; 1.52 mg/mL mono basic Na phosphate 2H$_2$O; 0.05 mg/mL dibasic Na phosphate 2H$_2$O; pH 5.3 ± 0.1 |
| 11 | 50.00 mg/mL active; 5.165 mg/mL NaCl; 19.5 mg/mL mannitol; 1 mg/mL PS80; 1.52 mg/mL mono basic Na phosphate 2H$_2$O; 0.05 mg/mL dibasic Na phosphate 2H$_2$O; pH 5.3 ± 0.1 |
| 12 | 50.00 mg/mL active; 5.165 mg/mL NaCl; 40.5 mg/mL trehalose 2H$_2$O; 1 mg/mL PS80; 1.07 mg/mL dibasic Na phosphate 2H$_2$O; 0.48 mg/mL succinic acid; pH 5.3 ± 0.1 |
| 13 | 50.00 mg/mL active; 5.165 mg/mL NaCl; 19.5 mg/mL mannitol; 1 mg/mL PS80; 1.07 mg/mL dibasic Na phosphate 2H$_2$O; 0.48 mg/mL succinic acid; pH 5.3 ± 0.1 |
| Originator | 50.00 mg/mL active; 6.165 mg/mL NaCl; 12.0 mg/mL mannitol; 1 mg/mL PS80; 0.86 mg/mL mono basic Na phosphate 2H$_2$O; 1.53 mg/mL dibasic Na phosphate 2H$_2$O; 0.31 mg/mL Na citrate 2H$_2$O; 1.31 mg/mL citric acid H$_2$O; pH 5.2 |

Figure 7:
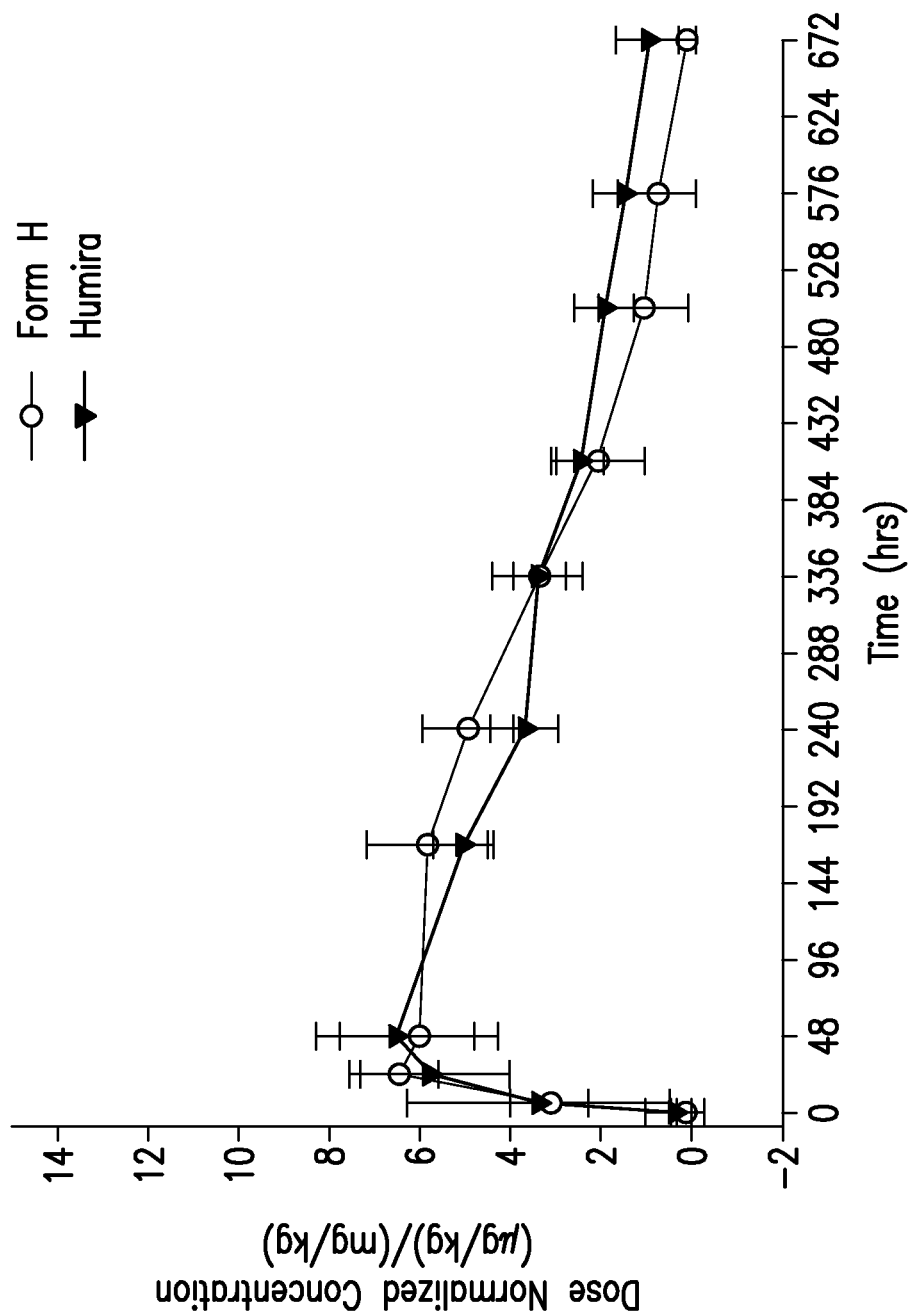
FIG. 7 provides a graphic representation of normalized serum concentration of biosimilar adalimumab (filled circles) administered in formulation H (defined in Table 7 as formulation #10) versus time (hours) compared to observed serum concentration of HUMIRA® (filled triangles) administered in the commercial formulation in rats via the subcutaneous route during a preliminary pharmacokinetic (PK) study.

Lead formulations were selected based on the biophysical and biochemical characterization and multi-step animal PK studies. Rodent and primate models were utilized to screen formulations. Table 7 provides list of formulations that have provided PK and AUC values that are superimposable with values of the originator product (see FIG. 7, which provides a graphic representation of normalized serum concentration of biosimiar adalimuab (filled circles) administered in Formulation H (which is defined as formulation #10 in Table 7) versus time (hours) compared to serum concentration of HUMIRA® (filled triangles) administered in the commercial formulation via the subcutaneous route during a preliminary pharmacokinetic (PK) study.

TABLE 7

Compositions of Lead Formulations

| # | Excipient | Amount, mg/mL |
|---|---|---|
| 10 | Sodium Phosphate Dibasic, Heptahydrate | 0.05 |
|  | Sodium Phosphate, Monobasic, Monohydrate | 1.35 |
|  | Sodium Chloride | 5.17 |
|  | Trehalose dihydrate | 40.50 |
|  | Polysorbate 80 | 1.00 |
|  | QS with WFI | 1.00 |
|  | Target pH 5.3 | |
| 11 | Sodium Phosphate Dibasic, Heptahydrate | 0.05 |
|  | Sodium Phosphate, Monobasic, Monohydrate | 1.35 |
|  | Sodium Chloride | 5.17 |
|  | Mannitol | 19.50 |
|  | Polysorbate 80 | 1.00 |
|  | QS with WFI | 1.00 |
|  | Target pH 5.3 | |
| 12 | Sodium Phosphate Dibasic, Heptahydrate | 1.62 |
|  | Succinic acid | 0.50 |
|  | Sodium Chloride | 5.17 |
|  | Trehalose dihydrate | 40.50 |
|  | Polysorbate 80 | 1.00 |
|  | QS with WFI | 1.00 |
|  | Target pH 5.3 | |
| 13 | Sodium Phosphate Dibasic, Heptahydrate | 1.62 |
|  | Succinic acid | 0.50 |
|  | Sodium Chloride | 5.17 |
|  | Mannitol | 19.50 |
|  | Polysorbate 80 | 1.00 |
|  | QS with WFI | 1.00 |
|  | Target pH 5.3 | |

All of the above demonstrates that stability of biosimilar adalimumab as analyzed by $UV_{280}$, MFI, Size Exclusion Chromatography (HP-SEC), Ion Exchange Chromatography (HP-IEX), Dynamic Light Scattering (DLS), Differential Scanning calorimetry (DSC) and Opalescence.

As such, liquid formulations containing pH buffered solution at a pH of between about 5.4 and 5.6 comprising phosphate or a phosphate-succinate buffer species, sodium chloride, a stabilizer, and a surfactant provide novel alternative liquid formulations for long-term storage of adalimumab-containing solutions.

Other embodiments are within the following claims. While several embodiments have been shown and described, various modifications may be made without departing from the spirit and scope of the present invention.

REFERENCES

Harris, R. J., et al., Commercial Manufacturing Scale Formulation and Analytical Characterization of Therapeutic Recombinant Antibodies, Drug Development Research 61: 137-154 (2004)

Wang, Wei, Instability, Stabilization, and Formulation of Liquid Protein Pharmaceuticals, International Journal of Pharmaceutics 185:129-188 (1999)

Barrera, P., et al., Effects of treatment with a fully human anti-tumor necrosis factor α monoclonal antibody on the local and systemic homeostasis of interleukin 1 and TNFα in patients with rheumatoid arthritis, Ann. Rheum. Dis. 60: 660-669 (2001)

What is claimed:

1. A stable liquid aqueous pharmaceutical formulation comprising:
   Adalimumab;
   0.05 mg/ml Sodium Phosphate Dibasic, Heptahydrate;
   1.35 mg/ml Sodium Phosphate, Monobasic, Monohydrate;
   5.17 mg/ml Sodium Chloride;
   40.50 mg/ml Trehalose dihydrate;
   1.00 mg/ml Polysorbate 80; and
   water,
   having a pH of 5.3.

2. A stable liquid aqueous pharmaceutical formulation comprising:
   adalimumab;
   0.05 mg/ml Sodium Phosphate Dibasic, Heptahydrate;
   1.35 mg/ml Sodium Phosphate, Monobasic, Monohydrate;
   5.17 mg/ml Sodium Chloride;
   19.50 mg/ml Mannitol;
   1.00 mg/ml Polysorbate 80; and
   water;
   having a pH of 5.3.

3. A stable liquid aqueous pharmaceutical formulation comprising:
   adalimumab;
   1.62 mg/ml Sodium Phosphate Dibasic, Heptahydrate;
   0.50 mg/ml Succinic acid;
   5.17 mg/ml Sodium Chloride;
   40.50 mg/ml Trehalose dihydrate;
   1.00 mg/ml Polysorbate 80; and
   water,
   having a pH of 5.3.

4. A stable liquid aqueous pharmaceutical formulation comprising:
   adalimumab;
   1.62 mg/ml Sodium Phosphate Dibasic, Heptahydrate;
   0.50 mg/ml Succinic acid;
   5.17 mg/ml Sodium Chloride
   19.50 mg/ml Mannitol;
   1.00 mg/ml Polysorbate 80; and
   water,
   having a pH of 5.3.

* * * * *